US007842500B2

(12) United States Patent
Suzuki et al.

(10) Patent No.: US 7,842,500 B2

(45) Date of Patent: Nov. 30, 2010

(54) ANTI-HEPARAN SULFATE ANTIBODY, METHOD FOR DETECTION OF HEPARAN SULFATE, AND KIT FOR DETECTION OF HEPARAN SULFATE

(75) Inventors: Kiyoshi Suzuki, Tokyo (JP); Takeshi Ishimaru, Tokyo (JP); Koji Yamamoto, Tokyo (JP)

(73) Assignee: Seikagaku Corporation, Chiyoda-ku, Tokyo (JP)

( * ) Notice: Subject to any disclaimer, the term of this patent is extended or adjusted under 35 U.S.C. 154(b) by 547 days.

(21) Appl. No.: 11/909,956

(22) PCT Filed: Mar. 31, 2006

(86) PCT No.: PCT/JP2006/306908

§ 371 (c)(1),
(2), (4) Date: Sep. 27, 2007

(87) PCT Pub. No.: WO2006/106950

PCT Pub. Date: Oct. 12, 2006

(65) Prior Publication Data

US 2009/0136964 A1 May 28, 2009

(30) Foreign Application Priority Data

Mar. 31, 2005 (JP) ............................ 2005-104920
Jul. 15, 2005 (JP) ............................ 2005-207525
Oct. 21, 2005 (JP) ............................ 2005-307253

(51) Int. Cl.
*C07K 16/12* (2006.01)
*C07K 16/18* (2006.01)
*C12N 5/20* (2006.01)
*C12P 21/08* (2006.01)
*G01N 33/53* (2006.01)
*G01N 33/569* (2006.01)
*G01N 33/577* (2006.01)

(52) U.S. Cl. ....................... 435/329; 435/7.1; 435/7.21; 435/7.37; 435/7.92; 435/7.93; 435/7.94; 435/7.95; 435/38; 435/40.5; 435/40.51; 435/40.52; 435/70.21; 435/452; 435/340; 435/252.33; 435/975; 436/501; 436/518; 436/543; 436/548; 530/387.5; 530/388.2; 530/388.4; 530/391.1

(58) Field of Classification Search .................. 435/7.1, 435/7.21, 7.37, 7.92, 7.93, 7.94, 7.95, 38, 435/40.5, 40.51, 40.52, 70.21, 72, 452, 329, 435/340, 252.33, 975; 436/501, 518, 543, 436/548; 530/387.5, 388.2, 388.4, 389.5, 530/391.1

See application file for complete search history.

(56) References Cited

U.S. PATENT DOCUMENTS 4,356,170 A * 10/1982 Jennings et al. .......... 424/194.1
4,830,852 A * 5/1989 Marburg et al. .......... 424/165.1
5,250,519 A * 10/1993 Conrad et al. ................. 514/56
5,296,471 A * 3/1994 Holme et al. ................. 514/56

FOREIGN PATENT DOCUMENTS

JP 2004-018840 * 1/2004

OTHER PUBLICATIONS

Kröncke et al., 1990. Expression of the *Escherichia coli* K5 capsular antigen: immunoelectron microscopic and biochemical studies with recombinant *E. coli*. J. Bacteriol. 172: 1085-1091.*

Hellström et al., 1985. In Monoclonal Antibodies for Cancer Detection and Therapy (Baldwin et al, eds.), Academic Press, London. p. 20.*

Kure et al., 1986. A syngeneic monoclonal antibody to murine Meth-A sarcoma (HepSS-1) recognizes heparan sulfate glycosaminoglycan (HS-GAG): cell density and transformation dependent alteration in cell surface HS-GAG defined by HepSS-1. J. Immunol. 137: 3900-3908.*

Suzuki, et al. "Generation and Characterization of a Series of Monoclonal Antibodies that Specifically Recognize [HexA(±2S)-GlcNAc]n Epitopes in Heparan Sulfate," *Glycoconjugate Journal*, vol. 25, No. 8, pp. 703-712, Nov. 2008.

Supplementary European Search Report dated Nov. 13, 2008.

van den Born, et al. "A Monoclonal Antibody Against GBM Heparan Sulfate Induces an Acute Selective Proteinuria in Rats," *Kidney International*, vol. 41, Nol. 1, pp. 115-123, 1992.

Peters, H., et al., Monoclonal Antibodies to Enterobacterial Common Antigen and to *Escherichia coli* Lipopolysaccharide Outer Core: Demonstration of an Antigenic Determinant Shared by Enterobacterial Common Antigen and *E. coli* K5 Capsular Polysaccharide, *Infection and Immunity*, vol. 50, No. 2, Nov. 1985, pp. 459-466.

Vann, Willie F., et al., The Structure of the Capsular Polysaccharide (K5 Antigen) of Urinary-Tract-Infective *Escherichia coli* 010:K5:H4, *Eur. J. Biochem*., vol. 116, 1981, pp. 359-364.

Van Den Born, Jacob, et al., N-Acetylated Domains in Heparan Sulfates Revealed by a Monoclonal Antibody against the *Escherichia coli* K5 Capsular Polysaccharide, *The Journal of Biological Chemistry*, vol. 271, 1996, pp. 22802-22809.

Van Den Born, Jacob, et al., Presence of N-Unsubstituted Glucosamine Units in Native Heparan Sulfate Revealed by a Monoclonal Antibody, *The Journal of Biological Chemistry*, vol. 270, No. 52, 1995, pp. 31303-31309.

Cheng, F., et al., Nitric Oxide-dependent Processing of Heparan Sulfate in Recycling S-Nitrosylated Glypican-1 Takes Place in Caveolin-1-containing Endosomes, *The Journal of Biological Chemistry*, vol. 277, No. 46, 2002, pp. 44431-44439.

(Continued)

*Primary Examiner*—Shafiqul Haq
*Assistant Examiner*—James L Grun
(74) *Attorney, Agent, or Firm*—Knobbe, Martens, Olson & Bear, LLP

(57) ABSTRACT

An antibody which reacts with N-acetylheparosan and heparan sulfate that is derived from bovine kidney but does not substantially react with heparan sulfate derived from a murine Engelbreath-Holm-Swarn tumor tissue, the antibody being produced with a hybridoma which is prepared using a substance composed of a protein and N-acetylheparosan bound to the protein.

5 Claims, 21 Drawing Sheets

OTHER PUBLICATIONS

David, Guido, et al., Developmental Changes in Heparan Sulfate Expression: In Situ Detection with mAbs, *The Journal of Cell Biology*, vol. 119, No. 4, Nov. 1992, pp. 961-975.

Matic, Maja, et al., Monoclonal Antibody to Heparan Sulfate from Autoimmune Tight Skin (TSK) Mice Binds to the Endothelial Cell Surface, *Immunological Investigations*, vol. 26, No. 3, 1997, pp. 371-381.

* cited by examiner (a)

(b)

(c)

(A)

(B)

(C)

ANTI-HEPARAN SULFATE ANTIBODY, METHOD FOR DETECTION OF HEPARAN SULFATE, AND KIT FOR DETECTION OF HEPARAN SULFATE

RELATED APPLICATIONS

This application is the U.S. National Phase under 35 U.S.C. §371 of International Application PCT/JP2006/306908, filed Mar. 31, 2006, which was published in a non-English language, which claims priority to JP 2005-104920, filed Mar. 31, 2005, JP 2005-207525, filed Jul. 15, 2005, and JP 2005-307253, filed Oct. 21, 2005.

TECHNICAL FIELD

The present invention relates to a novel anti-heparan sulfate antibody which reacts with N-acetylheparosan and heparan sulfate derived from bovine kidney but does not substantially react with heparan sulfate derived from a mouse Engelbreth-Holm-Swarm tumor tissue, a method of detecting heparan sulfate using the same, and a kit for detecting heparan sulfate.

BACKGROUND ART

Abbreviations to be used in this description are as follows.

2DSH: 2-O-desulfated HEP

2SH: (6-O.N)-desulfated-N-acetylated HEP

6DSH: 6-O-desulfated HEP

6SH: (2-O.N)-desulfated-N-acetylated HEP

Ac-2DSH: N-acetylated 2DSH

Ac-6DSH: N-acetylated 6DSH

Ac-NAH: N-acetylated NAH

Ac-NSH: N-acetylated NSH

CDSH: Completely desulfated-N-acetylated HEP

Ch: Chondroitin

CS-A(S): Chondroitin sulfate A derived from shark

CS-A(W): Chondroitin sulfate A derived from whale

CS-A: Chondroitin sulfate A

CS-B: Chondroitin sulfate B

CS-C: Chondroitin sulfate C

CS-D: Chondroitin sulfate D

CS-E: Chondroitin sulfate E

EHS-HS: Heparan sulfate derived from Engelbreth-Holm-Swarm tumor tissue

GAG: Glycosaminoglycan

HA: Hyaluronic acid

HEP: Heparin

HS: Heparan sulfate

HSPG: Proteoglycan-heparan sulfate

IdoA: L-iduronic acid

KS: keratan sulfate

NAc-HEP: N-acetylated HEP

NAH: N-acetyl heparosan

NDST: Glucosaminyl N-deacetylase/N-sulfotransferase $NH_2$-2SH: (6-O.N)-desulfated HEP $NH_2$-6SH: (2-O.N)-desulfated HEP $NH_2$—CDSH: Completely desulfated HEP $NH_2$—HEP: N-desulfated HEP NSH: (2-O.6-O)-desulfated HEP In this description, D-glucosamine residue is represented as $GlcNH_2$; hexuronic acid residue is represented as HexA; N-sulfated-D-glucosamine residue is represented as GlcNS; D-glucuronic acid residue is represented as GlcA; N-acetyl-D-glucosamine residue is represented as GlcNAc; and partially de-acetylated NAH is represented as PDNAc-NAH.

HS and HEP, which are kinds of GAGs, are acidic polysaccharides having a disaccharide-repeated structure containing a D-glucosamine residue and a hexuronic acid (GlcA or IdoA) residue as a basic sugar chain structure. In addition, they are modified by O-sulfation, N-sulfation, or N-acetylation to various degrees. HS is present as HSPG in cell surfaces of almost all animals (Non-patent Document 1), and is a major component of an extracellular matrix.

On the other hand, HEP is localized in a mucosal and a granule in a mast cell. As results of in vitro experiments, it has been revealed that HEP binds to many bioactive proteins (hereinafter, referred to as "HEP-binding proteins" or "HBPs") and that the functions of such HBPs are regulated by binding HEP. For example, HEP is considered to stabilize HBPs such as fibroblast growth factors, hepatocyte growth factor, etc., and to act as a cofactor or a co-receptor, thereby controlling cell proliferation. Further, the same results were confirmed in the experiments using HS. The structure of HEP that binds to each bioactive HBP is not uniform, and the importance of the degree of sulfation or site-specific sulfation is being recognized.

A major ligand of HBPs in vivo is considered to be not HEP but HS. That is, HS is considered to regulate the above-mentioned various biological reactions. Therefore, HS that is widely present in animal bodies and has various functions is important component for animals and human. From biological and medical points of view, it is very important to acquire qualitative and quantitative method for precisely detecting HS. Accordingly, a monoclonal antibody against HS may be a unique detection reagent.

Because of the aforementioned reasons, many reports on production of antibodies using HS or HEP as an antigen have been made in recent years. mAb HepSS-1 and mAb F58-10E4, which are monoclonal antibodies that recognize an N-sulfated glucosamine unit of HS (-[HexA-GlcNS]-), are commercially available and widely used.

When the structure of HS is analyzed in accordance with the method of "2.8 Structural analysis using degrading enzyme of glycosaminoglycan and HPLC in combination" described in Non-patent Document 2, it is easily understood that a major component disaccharide of HS is a nonsulfated disaccharide, GlcA-GlcNAc. The ratio reaches 50 to 60% although it depends on an organ from which HS is isolated. That is, the major structure of HS is an N-acetylglucosamine unit (-[GlcA-GlcNAc]-).

Meanwhile, in a certain disease such as diabetes, NDST activity that catalyzes a first step of the sulfation reaction of HS and HEP is decreased, resulting in increase in the ratio of an N-acetylglucosamine unit (Non-patent Document 3). Further, HS derived from kidney is known to contain a glucosamine unit (-[GlcA-$GlcNH_2$]-) (Non-patent Document 4).

Therefore, in order to distinguish HS derived from kidney from HSs derived from other organs, it is desirable to use an antibody that specifically recognizes a structure present in HS derived from kidney, that is, a glucosamine unit. Accordingly, detection/quantification of the N-acetylglucosamine unit or glucosamine unit, which forms a nonsulfated domain of HS, is as important as detection/quantification of a sulfated domain.

However, monoclonal antibodies that recognize the glucosamine unit or N-acetylglucosamine unit, which form a nonsulfated domain of HS, are only mAb JM403 and mAb 865 (Non-patent Documents 4 to 7), respectively.

mAb JM-403, which recognizes a glucosamine unit of HS, has been prepared from a mouse that was immunized with HSPG purified from rat glomerulus by van den Born, J. et al. van den Born, J. et al. have reported that HS contains 2 to 3 glucosamine units in average, and that the reactivity of the antibody disappears by acetylation of HS. They have also reported that the antibody does not react with NAH but react with de-N-acetylated NAH more strongly as compared to HS. In addition, they have reported that an N-sulfated glucosamine unit present in HS does not affect the reactivity of the antibody, but an O-sulfated structure or an IdoA structure inhibits the reactivity of the antibody (Non-patent Document 8).

On the other hand, mAb 865, which recognizes an N-acetylglucosamine unit of HS, was originally obtained as an antibody against enterobacterial common antigen (anti-ECA) by Peters, H. et al., and is cross-reactive to a capsular polysaccharide of *Escherichia coli* K5 (hereinafter, referred to as "NAH"). van den Born, J. et al. has reported that the antibody does not react with sulfated NAH or N-deacetylated NAH and its epitope is an N-acetylglucosamine unit of 18 sugars or more. Meanwhile, the reactivity of the antibody to HS is 1/3,000 or less than that to NAH (Non-patent Document 7), and it has been reported that the antibody reacts with mouse EHS-HS, which has high sulfation degree as compared to normal HS.

Mouse EHS-HS is HS with high sulfation degree. Therefore, an antibody capable of reacting with mouse EHS-HS reacts with HS of high sulfation degree, so the antibody is considered to have relatively low specificity to the antigen. As described above, an antibody that recognizes nonsulfated region containing N-acetylglucosamine units, glucosamine units, and the like of HS but does not react with mouse EHS-HS was not known, and therefore such an antibody has been desired.

Non-patent Document 1: Biochemistry, 10, 20 1445 (1971)

Non-patent Document 2: Shin Seikagaku Jikken Koza 3, Carbohydrates II (published by Tokyo Kagaku Dojin Co., Ltd., 1991) p. 49-62

Non-patent Document 3: Diabetes, 40, 1449 (1991)

Non-patent Document 4: Kidney Int., 41, 115 (1992)

Non-patent Document 5: J. Biol. Chem., 270, 31303 (1995)

Non-patent Document 6: Infect. Immun., 50, 459 (1985)

Non-patent Document 7: J. Biol. Chem., 271, 22802 (1996)

Non-patent Document 8: J. Biol. Chem., 270, 31303 (1995)

DISCLOSURE OF THE INVENTION

An object of the present invention is to provide an antibody that can be suitably used in detection of HS or NAH in a sample. In particular, an object of the present invention is to provide an antibody that specifically recognizes nonsulfated region consisting of N-acetylglucosamine units or glucosamine units.

In order to solve the aforementioned objects, the inventors of the present invention attempted to produce a novel anti-GAG antibody using a substance prepared by binding a protein to NAH as an antigen.

NAH which has been used by the inventors of the present invention to produce the antigen is an acidic polysaccharide mainly composed of an N-acetylglucosamine unit (Eur. J. Biochem., 116, 359-364 (1981)). The structure of NAH prepared in accordance with "N-acetylheparosan fraction and method for producing the same" described in JP 2004-018840 A was analyzed by the method "Structural analysis using degrading enzyme of glycosaminoglycan and HPLC in combination" described above. As a result, it was found that 99.5% or more of the NAH is composed of N-acetylglucosamine units but glucosamine units (([GlcA-GlcNH$_2$])) are also contained as a part of the NAH. Therefore, the inventors of the present invention considered that the prepared NAH has excellent properties as an antigenic substance for producing an antibody against NAH and an antibody against N-acetylglucosamine units or glucosamine units of HS. The inventors of the present invention have made extensive studies and have succeeded in producing an antibody that reacts with NAH and an antibody that recognizes N-acetylglucosamine units or glucosamine units of HS. Further, they have discovered that the antibody does not substantially react with mouse EHS-HS, thereby completed the present invention.

That is, the present invention provides the followings:

(1) An antibody, which reacts with N-acetylheparosan and heparan sulfate derived from bovine kidney, but does not substantially react with heparan sulfate derived from a mouse Engelbreth-Holm-Swarm tumor tissue.

(2) The antibody according to (1), which recognizes nonsulfated region in the N-acetylheparosan and the heparan sulfate derived from bovine kidney.

(3) The antibody according to (2), wherein the nonsulfated region consist of N-acetylglucosamine units or glucosamine units.

(4) The antibody according to any one of (1) to (3), wherein a ratio of the reactivity against N-acetylheparosan to the reactivity against heparan sulfate derived from bovine kidney is 10:2 to 10:20.

(5) The antibody according to any one of (1) to (4), which does not substantially react with hyaluronic acid.

(6) The antibody according to any one of (1) to (5), which does not substantially react with heparin or desulfated heparins.

(7) The antibody according to any one of (1) to (6), which does not substantially react with chondroitin, chondroitin sulfate-A, chondroitin sulfate-B, chondroitin sulfate-C, chondroitin sulfate-D, chondroitin sulfate-E, or keratan sulfate.

(8) The antibody according to any one of (1) to (7), which is a monoclonal antibody.

(9) The antibody according to any one of (1) to (7), which is a monoclonal antibody produced by a hybridoma formed by cell fusion of: a lymphocyte that is derived from a mammal immunized with a substance obtained by binding a protein to N-acetylheparosan as an antigen; and a myeloma cell derived from a mammal.

(10) The antibody according to (9), wherein the lymphocyte and myeloma cell are derived from mouse.

(11) A monoclonal antibody, which is produced by the hybridoma having Deposition number of FERM BP-10534, FERM BP-10535, or FERM BP-10536.

(12) A substance, which is obtained by chemically binding a protein to N-acetylheparosan, and has antigenicity that enables production of an antibody which reacts with N-acetylheparosan.

(13) A hybridoma, which is formed by cell fusion of: a lymphocyte that is derived from a mammal immunized with a substance obtained by chemically binding a protein to N-acetylheparosan as an antigen; and a myeloma cell derived from a mammal.

(14) The hybridoma according to (13), wherein the lymphocyte and myeloma cell are derived from mouse.

(15) A hybridoma which has the Deposition number of FERM BP-10534, FERM BP-10535, or FERM BP-10536.

(16) A method of detecting heparan sulfate or N-acetylheparosan in a sample, wherein the antibody according to any one of (1) to (11) is used.

(17) A kit for detecting heparan sulfate or N-acetylheparosan in a sample, comprising at least one antibody according to any one of (1) to (11).

(18) The detecting method according to (16), wherein the sample is derived from a source selected from the group consisting of body fluids, cells, tissues, and cultures of cells or microorganisms.

(19) The detection kit according to (17), wherein the sample is derived from a source selected from the group consisting of body fluids, cells, tissues, and cultivated cells or microorganisms.

DESCRIPTION OF THE PREFERRED EMBODIMENTS

Figure 1:
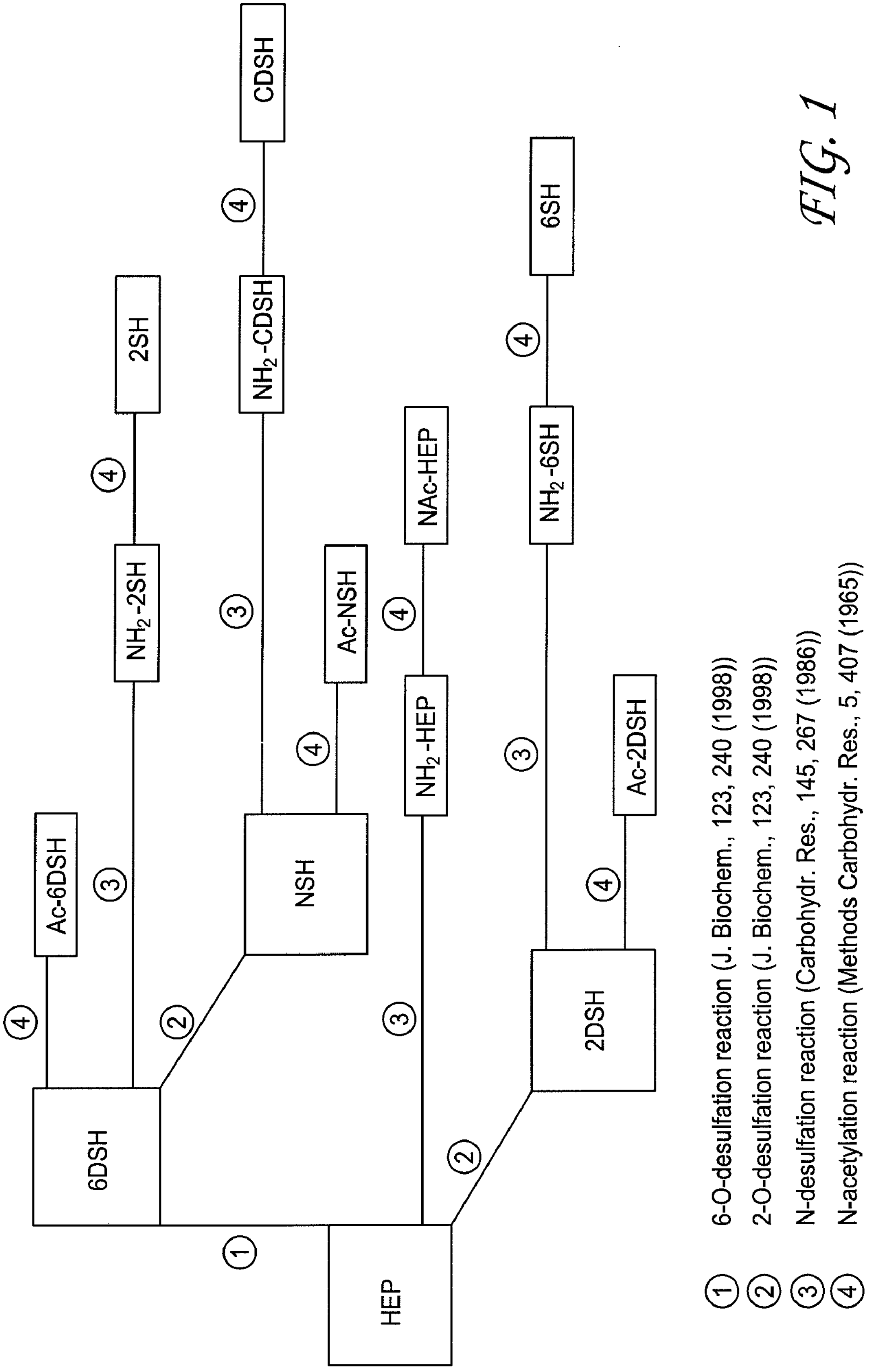
FIG. 1 A diagram showing a method of producing the modified HEPs.

Hereinafter, the present invention will be described in more detail.

The present invention provides antibodies that react with NAH and bovine kidney HS but does not substantially react with EHS-HS (hereinafter, referred to as "antibody of the present invention").

NAH is a capsular polysaccharide isolated from *Escherichia coli* K5 and an acidic polysaccharide having an N-acetylglucosamine unit as a basic sugar chain structure (Eur. J. Biochem., 116, 359-364 (1981)). NAH can be prepared by, for example, the method described in Reference Example 1 below.

As shown in the results of the analysis of disaccharide compositions described in Reference Example 3 below, the bovine kidney HS is HS in which about 35% of N-positions of D-glucosamine residues are sulfated. Such bovine kidney HS can be purified by treating acetone-defatted bovine kidney with alkaline extraction, protease digestion, removal of nucleic acids, alcohol fractionation, and chondroitinase ABC treatment, followed by chromatography in accordance with the method by Schiller, S. et al. (Lanber, A. et al., Biochim. Biophys. Acta., 29, 443 (1958), Schiller, S. et al., J. Biol. Chem., 236, 983 (1961), Iverius, P. H., Biochem. J. 124, 677 (1971)). A specific example of bovine kidney HS includes the HS of research reagent, code number 400700, manufactured by Seikagaku Corporation.

Mouse EHS-HS (heparan sulfate derived from an Engelbreth-Holm-Swarm tumor tissue) is HS isolated from mouse EHS (Engelbreth-Holm-Swarm) tumor tissue. Preparation of HS from mouse EHS tumor tissue can be performed in accordance with the method described in JP 07-53756 B, for example. As shown in the results of the analysis of disaccharide compositions described in Reference Example 3 below, such EHS-HS is HS in which about 65% of N-positions of D-glucosamine residues are sulfated.

In the present invention, if not specified, the term "reaction" means an immunological reaction or an antigen-antibody reaction, and the reactivity of an antibody to an antigen can be determined by, for example, the ELISA method, RIA method, plaque method, agglutination method, flow cytometry method, histological staining method, Western blotting method, etc. For example, if a reaction signal of the ELISA method using an antibody is enhanced in proportion to an increase in the concentration of an antigen, the antibody is considered to react with the antigen.

In this description, the phrase "does not substantially react" means that the reactivity of an antibody to an antigen provides no reaction signal or provides only an extremely slight reaction signal by the aforementioned method of determining the reactivity. In particular, with regard to the reactivity of the antibody of the present invention to EHS-HS, when the reactivity to EHS-HS is examined by setting conditions including reaction time, detection method, and concentration of an antigen in an antigen solution and concentration of an antibody in an antibody solution to be used for determination to the same conditions for sufficiently detecting the reactivity of the antibody of the present invention to NAH so as to achieve an absorbance difference of about 2.0 (the absorbance difference can be obtained by subtracting an absorbance obtained in a case of using a blank solution not containing the antibody of the present invention as a test solution from an absorbance in a case of determining the reactivity of the antibody of the present invention to the antigen using a solution containing the antibody of the present invention as a test solution. Refer to specific examples shown in Example 4 below.), if the reactivity of the antibody of the present invention to EHS-HS is 10% or less, more preferably 5% or less compared to that to NAH, the antibody is considered not to substantially react with EHS-HS. Specific examples of the conditions for detection may be any of the conditions for determination of reactivity of NAH33 antibody, NAH43 antibody, and NAH46 antibody in Example 4 shown below, which can be referred.

Meanwhile, the following description on the ratio of the reactivity of the antibody of the present invention against NAH to the reactivity against other GAGs or the like, such as a ratio of the reactivity against NAH to the reactivity against bovine kidney HS and a ratio of the reactivity against NAH to the reactivity against about 40% de-N-acetylated NAH, represents a ratio of the degrees of the reactivity in a case where the reactivity against NAH and other GAGs or the like are examined by setting conditions including reaction time, detection method, concentration of an antigen in an antigen solution and concentration of an antibody in an antibody solution to be used for determination to the same conditions for sufficiently detecting the reactivity of the antibody of the present invention to NAH so as to achieve an absorbance difference of about 2.0 as a detection result. Specific examples of the conditions in the detection may be any of the conditions in determination of reactivity of NAH33 antibody, NAH43 antibody, and NAH46 antibody in Example 4 shown below, which can be referred.

When the antibody of the present invention is NAH33 antibody, NAH43 antibody, or NAH46 antibody, methods of examining the reactivity of the antibody of the present invention to EHS-HS and the ratios of the reactivity of the antibody of the present invention against NAH to the reactivity against other GAGs or the like may be the method described in Example 4 shown below, which can be referred.

The antibodies of the present invention are not particularly limited as long as they react with NAH and bovine kidney HS and do not substantially react with EHS-HS. Therefore, the antibodies of the present invention may react with both NAH and HS derived from other than bovine kidney. HS that reacts with the antibody of the present invention contains a nonsulfated disaccharide obtained by the methods described in Examples shown below at a rate of preferably not less than about 40%, more preferably not less than about 50%.

The ratio of the reactivity of the antibody of the present invention against NAH to the reactivity of the antibody of the present invention against bovine kidney HS is preferably 10:2 to 10:20, more preferably 100:20 to 100:90.

Examples of the antibody include the following antibodies (i) and (ii).

(i) An antibody that achieves a ratio of the reactivity against NAH to the reactivity against bovine kidney HS of 100:30 to 100:50. In addition, an antibody that achieves the ratio of 100:35 to 100:45. Specific examples of such an antibody include the monoclonal antibodies produced by the hybridoma having Deposition Nos. FERM BP-10534 and FERM BP-10536 (also referred to as "NAH33 antibody" and "NAH46 antibody", respectively).

(ii) An antibody that achieves a ratio of the reactivity against NAH to the reactivity against bovine kidney HS of 100:60 to 100:90. In addition, an antibody that achieves the ratio of 100:70 to 100:80. Specific examples of such an antibody include the monoclonal antibody produced by the hybridoma having Deposition No. FERM BP-10535 (also referred to as "NAH43 antibody").

Meanwhile, the antibodies of the present invention are preferably antibodies that do not substantially react with HA. Examples of the HA include the HA described in Examples shown below. In addition, the antibodies of the present invention are preferably antibodies that do not substantially react with HEP or desulfated HEPs, more preferably antibodies that do not substantially react with HEP and desulfated HEPs. Examples of the HEPs include HEPs described in Examples shown below.

The desulfated HEPs are described in Examples shown below and selected from the group consisting of 6DSH, NSH, $NH_2$—HEP, $NH_2$-2SH, $NH_2$-6SH, $NH_2$—CDSH, NAc-HEP, 2SH, 6SH, CDSH, Ac-6DSH, and Ac-NSH. Further, the antibodies are preferably ones that do not substantially react with 2DSH and/or Ac-2DSH.

Further, the antibody of the present invention is preferably one that does not substantially react with GAG selected from the group consisting of Ch, CS-A, CS-B, CS-C, CS-D, CS-E, and KS, more preferably one that does not substantially react with Ch, CS-A, CS-B, CS-C, CS-D, CS-E, and KS. Examples of the GAGs include GAGs described in Examples shown below.

The antibody of the preset invention preferably has specific reactivity to de-N-acetylated NAH. Examples of the antibody include the following antibodies (iii) to (v).

(iii) An antibody that does not substantially react with about 40% de-N-acetylated NAH. In addition, the antibody is preferably one that does not substantially react with about 20% de-N-acetylated NAH, more preferably one that does not substantially react with about 10% de-N-acetylated NAH. Specific examples of such an antibody include the monoclonal antibody produced by the hybridoma having Deposition No. FERM BP-10534 (NAH33 antibody).

(iv) An antibody that achieves a ratio of the reactivity against NAH to the reactivity against about 40% de-N-acetylated NAH of 100:60 to 100:150. The ratio is more preferably 100:80 to 100:130, and particularly preferably about 100:110. Further, the antibody preferably achieves a ratio of the reactivity against NAH to the reactivity against about 20% de-N-acetylated NAH of 100:60 to 100:150, and preferably achieves a ratio of the reactivity against NAH to the reactivity against about 10% de-N-acetylated NAH of 100:60 to 100:100. Specific examples of such an antibody include the monoclonal antibody produced by the hybridoma having Deposition No. FERM BP-10535 (NAH43 antibody).

(v) An antibody that does not substantially react with about 40% de-N-acetylated NAH. The antibody preferably achieves a ratio of the reactivity against NAH to the reactivity against about 20% de-N-acetylated NAH of 100:10 to 100:50. Further, the antibody preferably achieves a ratio of the reactivity against NAH to the reactivity against about 10% de-N-acetylated NAH of 100:60 to 100:100. Specific examples of such an antibody include the monoclonal antibody produced by the hybridoma having Deposition No. FERM BP-10536 (NAH46 antibody).

For example, de-N-acetylated NAH can be prepared in accordance with the method described in "[Reference Example 1] 2. Preparation of PDNAc-NAH" shown below. In this description, the de-N-acetylation ratio (%) of de-N-acetylated NAH means a de-N-acetylation ratio obtained by the method described in "[Reference Example 1] 2. Preparation of PDNAc-NAH" shown below.

The antibodies of the present invention can recognize nonsulfated region in NAH and bovine kidney HS.

Specific examples of the nonsulfated region include a region composed of N-acetylglucosamine units or glucosamine units. Such nonsulfated region may comprise either one or both of the N-acetylglucosamine unit and glucosamine unit.

The kind of the antibody of the present invention is not particularly limited, and the antibody may be a polyclonal antibody but is preferably a monoclonal antibody. The monoclonal antibody may be a fragment thereof. Examples of the fragment of a monoclonal antibody include $F(ab')_2$ antibodies, Fab antibodies, short-chain antibodies (scFv), diabodies, and minibodies.

The immunoglobulin class of the monoclonal antibody is not particularly limited, but the class is preferably IgM, and more preferably IgM of κ-chain.

The monoclonal antibody can be obtained by, for example, producing a hybridoma by cell fusion of an antibody-producing cells (preferably lymphocytes) of a mammal (preferably a mouse) immunized with, as an antigen, a substance prepared by chemically binding a protein to NAH, and myeloma cells of a mammal (preferably a mouse), selecting a hybridoma that produces a monoclonal antibody having the above-mentioned properties from the resultant hybridoma, and collecting a monoclonal antibody from the culture supernatant of the hybridoma.

The antigenic substance to be used for producing the antibody is a substance that is obtained by chemically binding a protein to NAH and has the antigenicity that enables production of an antibody that reacts with NAH. The substance can be obtained by, for example, covalently binding NAH prepared by the method described in JP 2004-018840 A to a protein.

Hereinafter, a method of obtaining the antibodies of the present invention will be described in detail. However, the method of obtaining the antibodies of the present invention is not limited thereto.

The first step of obtaining the antibodies of the present invention is to establish novel monoclonal hybridoma capable of producing the antibodies. Specific details of the method of establishing the hybridoma will be described in Examples, and the method briefly includes the following three main steps:

1. immunization;
2. cell fusion; and
3. selection of hybridoma and cloning.

1. Immunization

In the present invention, NAH is preferably used as an antigen for the immunization step. In addition, the NAH is preferably chemically bound to a protein before use. The protein is preferably bovine serum albumin (hereinafter, referred to as "BSA") or hemocyanin (hereinafter, referred to as "KLH").

In the present invention, GAG or proteoglycan is preferably used as an antigen to be used for immunization, and NAH is more preferably used. In addition, they are preferably bound to a protein before use. For example, the mode of chemical bond of a protein and GAG or proteoglycan is not particularly limited, but it is preferably a covalent bond, more preferably a disulfide bond (hereinafter, referred to as "—SS—"). Specifically, for example, GAG is reductively aminated, and allowed to react with 5 mM N-succinimidyl-3-(2-pyridyldithio)propionate (hereinafter, referred to as "SPDP"), to thereby yield a 2-pyridyldithiopropynylated GAG. The resultant 2-pyridyldithiopropynylated GAG is reduced with a reductant such as dithiothreitol to yield thiolated GAG. In the same way as described above, a protein is allowed to react with SPDP, to thereby yield a 2-pyridyldithiopropynylated protein. After that, a solution of the thiolated GAG and a solution of the 2-pyridyldithiopropynylated protein are mixed to form an SS bond between the GAG and the protein, to thereby yield a GAG-SS-protein (hereinafter, referred to as "GAG antigen").

The animal to be immunized in the present invention is preferably a mammal such as pig, cow, mouse, or rat, and a mouse is particularly preferable because myeloma cells to be used as antibody-producing cells are preferably derived from a mouse. For example, immunization can be performed by subcutaneously-injecting the NAH antigen prepared by the aforementioned method to a mammal. The injection method is not limited thereto, and intraperitoneal injection or intravenous injection may be employed. In general, the immunization is performed in several times, and is preferably performed by administering an antigen together with an adjuvant. The adjuvant may be a substance that is expected to have an adjuvant effect, such as alum, dead tubercle bacilli, nucleic acid, complete Freund's adjuvant, or incomplete Freund's adjuvant, and in particular, TiterMAX Gold (manufactured by Sigma-Aldrich Co.) is preferable.

2. Cell Fusion

After final immunization, the lymph node or spleen is removed, and the resultant lymphocytes are used for cell fusion. On the other hand, a tumor cell strain to be used for cell fusion is preferably a myeloma cell, and in general, P3-NS-1/1-Ag4-1, P3-X63-Ag8-U1(P3 U1), P3-X63-Ag8-653, SP2/0-Ag14, etc. derived from BALB/c mouse may be used.

3. Selection of Hybridoma and Cloning

Selection of hybridoma and cloning may be performed by the following method. That is, a hybridoma that produces a desired antibody capable of reacting with NAH is selected from a culture supernatant of proliferating hybridoma by various analysis methods (such as the RIA method, plaque method, agglutination method, ELISA method, flow cytometry method, tissue staining method, and Western blotting method), and then the resultant hybridoma is cloned. Examples of the cloning method include fluorescent activated cell sorter (FACS) and a generally used method such as limiting dilution method. For example, the limiting dilution method is preferably performed so that one or less cell is present per well in a 96-well plate. In any case, cloning is preferably repeated twice so that an antibody is obtained as a monoclonal antibody.

The second step of obtaining the antibodies of the present invention is to produce anti-NAH monoclonal antibodies.

Examples of a method of producing an anti-NAH monoclonal antibody include a method of cultivating a resultant monoclonal cell in vitro in large scale and a method of cultivating a resultant monoclonal cell in vivo (in ascites), and the method can be selected depending on the purpose. A monoclonal antibody produced by a single hybridoma can be separated and purified from a cell culture solution or an ascites of a mouse transplanted with the hybridoma. Purification of an antibody from the crude antibody solution can be performed by an appropriate combination of general biochemical techniques such as salting-out, ion exchange, gel filtration, affinity chromatography, and electrophoresis.

Examples of a monoclonal antibody obtained as described above include a monoclonal antibody produced by the hybridoma named NAH33 (hereinafter, referred to as NAH33 antibody). The hybridoma was deposited at the International Patent Organism Depositary, National Institute of Advanced Industrial Science and Technology (Central 6, 1-1, Higashi 1-chome, Tsukuba-shi, Ibaraki-ken, 305-8566 Japan) under Deposition No. FERM P-20457 on Mar. 11, 2005. Then, it was transferred to the international deposit under Budapest Treaty under Deposition No. FERM BP-10534.

NAH33 antibody has the following reactivity. That is, the antibody reacts with NAH and bovine kidney HS and does not substantially react with mouse EHS-HS, HA, HEP, Ch, CS-A, CS-B, CS-C, CS-D, CS-E, KS, PDNAc-NAH (about 40% de-N-acetylated NAH, about 20% de-N-acetylated NAH, and about 10% de-N-acetylated NAH). The reactivity of the antibody to bovine kidney HS is about 40% as compared to that to NAH. Further, a ratio of the reactivity against NAH to the reactivity against Ac-NAH is about 1:1.

Examples of another monoclonal antibody obtained as described above include the monoclonal antibody produced by the hybridoma named NAH43 (hereinafter, referred to as NAH43 antibody). The hybridoma was deposited at the International Patent Organism Depositary, National Institute of Advanced Industrial Science and Technology (Central 6, 1-1, Higashi 1-chome, Tsukuba-shi, Ibaraki-ken, 305-8566 Japan) under Deposition No. FERM P-20458 on Mar. 11, 2005. Then, it was transferred to the international deposit under Budapest Treaty under Deposition No. FERM BP-10535.

NAH43 antibody has the following reactivity. That is, the antibody reacts with NAH and bovine kidney HS and does not substantially react with mouse EHS-HS, HA, HEP, Ch, CS-A, CS-B, CS-C, CS-D, CS-E, and KS. The reactivity of the antibody to bovine kidney HS is about 75% as compared to that to NAH. There is substantially no difference between the reactivity of the antibody to NAH and the reactivity of the antibody to about 20% de-N-acetylated NAH. That is, a ratio of the reactivity against NAH to the reactivity against about 40% de-N-acetylated NAH and ratio of the reactivity against NAH to the reactivity against about 20% de-N-acetylated NAH are each about 100:110. A ratio of the reactivity against NAH to the reactivity against about 10% de-N-acetylated NAH is about 100:80. Further, the reactivity to Ac-NAH is about 70% as compared to that to NAH.

Examples of another monoclonal antibody obtained as described above include the monoclonal antibody produced by the hybridoma named NAH46 (hereinafter, referred to as NAH46 antibody). The hybridoma NAH46 was deposited at the International Patent Organism Depositary, National Institute of Advanced Industrial Science and Technology (Central 6, 1-1, Higashi 1-chome, Tsukuba-shi, Ibaraki-ken, 305-8566 Japan) under Deposition No. FERM P-20459 on Mar. 11, 2005. Then, it was transferred to the international deposit under Budapest Treaty under Deposition No. FERM BP-10536.

NAH46 antibody has the following reactivity. That is, the antibody reacts with NAH and bovine kidney HS and does not substantially react with mouse EHS-HS, HA, HEP, Ch, CS-A, CS-B, CS-C, CS-D, CS-E, and KS. The reactivity of the antibody to bovine kidney HS is about 40% as compared to that to NAH. In addition, the antibody does not substantially react with about 40% de-N-acetylated NAH. The reactivity to about 20% de-N-acetylated NAH is about 40% as compared to that to NAH, and the reactivity to about 10% de-N-acetylated NAH is about 80% as compared to that to NAH. Further, a ratio of the reactivity against NAH to the reactivity against Ac-NAH is about 1:1.

The antibodies of the present invention can be used in detection of HS or NAH present in a sample. Therefore, the present invention provides a method of detecting HS or NAH present in a sample, characterized by using the antibody of the present invention.

The sample is not particularly limited as long as it contains or may contain HS or NAH. In this description, the phrase "contains HS or NAH" means that a sample may contain either one or both of HA and NAH. The sample is not particularly limited as long as it may contain HS or NAH, and examples of the origin of the sample include body fluids such as urine, blood, plasma, serum, synovial fluid, and marrow, secreted material, cells, tissues, organs, culture supernatants of animal and plant cells or microorganisms, and culture products such as cells themselves or bacterial cells themselves. The term "origin" means that the sample may be a purified product, an extracted product, a specimen, etc. derived from the above-mentioned origins, or may be any of the origins themselves.

In the case of using a tissue specimen as a sample, the detection method of the present invention may be performed using a general immunohistochemical staining method or the like, while in the case of using a body fluid as a sample, the method may be performed by using the ELISA method, RIA method, sandwich method, competition method, plaque method, agglutination method, flow cytometry method, and Western blotting method, or the like.

In the sandwich method, as in Example 7 shown below, the antibody of the present invention may be immobilized to a solid phase such as a plate as a primary antibody, or the antibody of the present invention may be labeled as a secondary antibody. Examples of the antibody of the present invention include NAH33 antibody, NAH43 antibody, and NAH46 antibody. A secondary antibody in the case of using the antibody of the present invention as a primary antibody, and a primary antibody in the case of using the antibody of the present invention as a secondary antibody are not particularly limited as long as they are capable of binding to HS or NAH to be detected, and examples thereof include antibodies such as mAb JM403 (hereinafter, referred to as "JM403") and mAb F58-10E4 (hereinafter, referred to as "10E4"). In addition, both the primary and secondary antibodies may be the antibodies of the present invention. In this case, the antibodies of the present invention may be used in an appropriate combination as the primary and secondary antibodies, and examples of the combination include: a combination of NAH33 antibody as a primary antibody and any one of NAH33 antibody, NAH43 antibody, and NAH46 antibody as a secondary antibody; a combination of NAH43 antibody as a primary antibody and any one of NAH33 antibody, NAH43 antibody, and NAH46 antibody as a secondary antibody; and a combination of NAH46 antibody as a primary antibody and any one of NAH33 antibody, NAH43 antibody, and NAH46 antibody as a secondary antibody.

According to a detection method of the present invention, it is possible to specifically detect HS or NAH that is present in a sample and is recognized by the antibody of the present invention by using the specificity of the reaction of the antibody of the present invention. Meanwhile, the detection method of the present invention can be applied to various purposes such as judgment of the presence or absence or the degree of canceration or inflammation in cells or tissues, determination of NAH or HA in a culture supernatant, or judgment of the presence or absence or the degree of various diseases, by using the specificity of the reaction of the antibody of the present invention.

Further, the present invention provides a kit for detecting HS or NAH present in a sample, which at least comprises the antibody of the present invention. According to the detection kit of the present invention, it is possible to easily implement the detection method of the present invention. Examples of the kit "which at least comprises the antibody of the present invention" include a kit comprising the antibody of the present invention itself (including the antibody of the present invention dissolved in a solution or the like) as a component, a kit comprising a solid phase immobilized with the antibody of the present invention as a component, and a kit comprising the antibody of the present invention labeled with an enzyme or the like as a component. In addition, the term "sample" has the same meaning as described above on the detection method of the present invention. Further, the detection kit may include, in addition to the antibody of the present invention, a secondary antibody, a reaction buffer, a washing solution, a reaction substrate, an HS standard solution, etc.

EXAMPLES

Hereinafter, the present invention will be described specifically by way of examples. However, the present invention is not limited thereto.

Reference Example 1

Preparation of NAH and PDNAc-NAH

1. Preparation of NAH

NAH was prepared by the fermentation method using *Escherichia coli* K5 (see JP 2004-018840 A). Characteristics of the resultant NAH are shown below. The weight-average molecular weight (Mw) and number-average molecular weight (Mn), which were determined by gel filtration chromatography using Shodex STANDARD P-82 kit (P-800; 788 kDa, P-400; 404 kDa, P-200; 210 kDa, P-100; 112 kDa, P-50; 47.3 kDa, P-20; 22.8 kDa, P-10; 11.8 kDa, and P-5; 5.9 kDa, Showa Denko K.K.) as molecular weight standard markers, were found to be 128,646 and 106,144, respectively, and the molecular weight dispersion degree (Mw/Mn) was found to be 1.212. The nucleic acid content determined by EtBr (ethidium bromide) colorimetric determination was found to be 0.09%. The protein content determined by the Lowry method (Lowry J. et al., J. Biol. Chem. 193, 265-275, (1951)) was found to be 2.38%. The number of moles of free amines determined by the 2,4,6-TNBS method (Biochemica et Biophysica Acta. (1967) 141, 358-365) was found to be 0.026 μM/mg.

2. Preparation of PDNAc-NAH

NAH prepared by the above-mentioned method was used to prepare PDNAc-NAH in accordance with the method by Shaklee, P. N. et al. (Biochem. J., 217, 187 (1984)). The deacetylation degree (%) was determined by using an amino acid quantification reagent, Fluoraldehyde™ Reagent Solution (Pierce Biotechnology). Specifically, 80 μl of a 50 μg/ml sample solution was dispensed into each test tube, and 800 μl of the above-mentioned reagent was added thereto, followed by determination of fluorescence (λex=340 nm, λem=455 nm) of the solution mixture. Glucosamine hydrochloride was used as a standard to calculate a concentration of glucosamine (μg/ml) in a sample solution based on fluorescence intensity. NAH is a polysaccharide comprising glucuronic acid and N-acetylglucosamine, so the concentration of N-acetylglucosamine in 50 μg/ml NAH is approximately 25 μg/ml. Therefore, a value of the calculated concentration of glucosamine was divided by a value of the approximate concentration of N-acetylglucosamine, and the resultant value was expressed in percentage, to thereby determine the deacetylation degree. The deacetylation degrees for different reaction time of the deacetylation reaction are shown in the following table.

TABLE 1

| Abbreviations | Time for deacetylation reaction (minutes) | Degree of deacetylation (%) |
|---|---|---|
| PDNAc-NAH30 | 30 | 12.5 |
| PDNAc-NAH60 | 60 | 22.9 |
| PDNAc-NAH120 | 120 | 40.2 |

Reference Example 2

Preparation of Biotin-Labeled Gag (Hereinafter Referred to as "Bi-GAG")

1. Biotin Labeling of Natural GAGs

Natural GAGs (NAH, HS, HA, HEP, Ch, CS-A(S), CS-A (W), CS-B, CS-C, CS-D, CS-E, and KS) were dissolved in 0.1 M MES buffer (pH 5.5) to prepare 10 mg/ml GAG solutions. 25 μl of 20 mM biotin-LC-hydrazide (manufactured by Pierce Biotechnology) dissolved in dimethylsulfoxide (manufactured by Wako Pure Chemical Industries, Ltd.) was added to 1 ml of each GAG solution. Subsequently, 12.5 μl of a 100 mg/ml EDC (manufactured by Pierce Biotechnology) solution prepared with 0.1 M MES buffer (pH 5.5) was added thereto. The mixture was mixed well, and then allowed to react with stirring at normal temperature (15° C. to 25° C.) for 16 to 24 hours. After completion of the reaction, the reaction products were dialyzed by using a dialysis membrane (cutoff molecular weight: 10,000 or less) against phosphate buffered saline (pH 7.2 to 7.5, containing no divalent ions such as calcium ion: hereinafter, referred to as "PBS(−)") as dialysis solution, to thereby sufficiently remove free biotin. After completion of dialysis, the concentration of Bi-GAG was adjusted to 5 mg/ml, followed by freeze preservation.

The above-mentioned method yielded biotin-labeled natural GAGs (Bi-NAH, Bi-HS, Bi-HA, Bi-HEP, Bi-Ch, Bi-CS-A(S), Bi-CS-A(W), Bi-CS-B, Bi-CS-C, Bi-CS-D, Bi-CS-E, and Bi-KS).

NAH is the product prepared in Reference Example 1, HEP is a product manufactured by SPL (derived from pig intestines), and other GAGs are products manufacture by Seikagaku Corporation as follows: HA (derived from pig skin), Ch (obtained by treating CS-C shown below with acidic methanol), CS-A(S) (derived from sturgeon notochord), CS-A(W) (derived from whale cartilage), CS-B (derived from pig skin), CS-C (derived from shark cartilage), CS-D (derived from shark cartilage), CS-E (derived from squid cartilage), and KS (derived from bovine cornea). HS was bovine kidney HS manufactured by Seikagaku Corporation. Hereinafter, in the examples, it is simply referred to as bovine kidney HS.

2. Biotin Labeling of PDNAc-NAH and Chemically-Modified Gag

PDNAc-NAH30, PDNAc-NAH60, PDNAc-NAH120 described in Reference Example 1 were used as starting materials to perform biotin labeling by the same method as described above.

Meanwhile, 12 kinds of products obtained from HEP as a starting material by site-specific desulfation and products obtained by N-acetylation of NAH were prepared as chemically-modified GAGs and labeled with biotin by the same method as described above. A method of preparing chemically-modified GAGs will be described below.

6DSH, 2DSH, and NSH were prepared by the method of Kariya, Y. et al. (Kariya, Y. et al., J. Biochem., 123, 240 (1998)).

Pyridinium salts of HEP, 6DSH, 2DSH and NSH as starting materials were prepared and de-N-acetylated in accordance with the method of Ayotte, L., et al. (Ayotte, L., et al., Carbohydr. Res., 145, 267 (1986)), to thereby yield $NH_2$—HEP, $NH_2$-2SH, $NH_2$-6SH, and $NH_2$—CDSH, respectively.

$NH_2$—HEP, $NH_2$-2SH, $NH_2$-6SH, $NH_2$—CDSH, 6DSH, NSH and NAH as starting materials were N-acetylated in accordance with the method of Danishefsky, I., et al. (Danishefsky, I., et al., Methods Carbohydr. Res., 5, 407 (1965)), to thereby yield NAc-HEP, 2SH, 6SH, CDSH, Ac-6DSH, Ac-NSH, and Ac-NAH, respectively. The flowchart of the method of producing the various modified HEPs is shown in FIG. 1.

Reference Example 3

Analysis of Disaccharide Compositions of Mouse EHS-HS and Bovine Kidney HS

The disaccharide compositions of mouse EHS-HS and bovine kidney HS were analyzed. The disaccharide compositions represent the ratio of the above-mentioned disaccharides having the above-mentioned specific structures to the amount of unsaturated disaccharides with identifiable structure obtained by the disaccharide composition analysis with enzyme digestion in Test Method 1 shown below (the total mol % of ΔDiHS-0S, ΔDiHS-NS, ΔDiHS-6S, ΔDiHS-US, ΔDiHS-di(6,N)S, ΔDiHS-di(U,N)S, ΔDiHS-di(U,6)S, and ΔdiHS-tri(U,6,N)S) defined as 100%. The numerical values reflect sulfation of a sulfated polysaccharide before digestion.

In this description, the designations of the disaccharide compositions represent the followings.

TABLE 2

[Chemical formula 1]

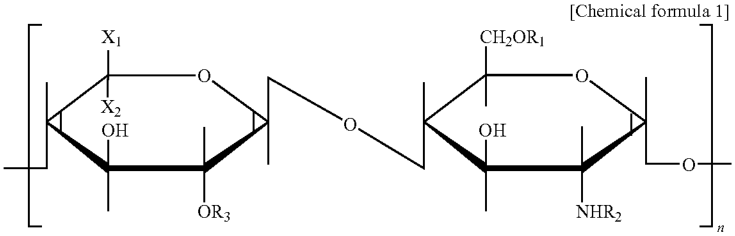

$R_1$, $R_3$ = $SO_3H$/H
$R_2$ = $SO_3H$/Ac
($X_1$, $X_2$) = (COOH, H) or H, COOH

| | Substituents in the above-mentioned structural formula | | |
|---|---|---|---|
| Unsaturated disaccharides | $R^1$ | $R^2$ | $R^3$ |
| ΔdiHS-0S | H | $COCH_3$ | H |
| ΔdiHS-NS | H | $SO_3H$ | H |
| ΔdiHS-6S | $SO_3H$ | $COCH_3$ | H |
| ΔdiHS-US | H | $COCH_3$ | $SO_3H$ |
| ΔdiHS-di(6,N)S | $SO_3H$ | $SO_3H$ | H |
| ΔdiHS-di(U,N)S | H | $SO_3H$ | $SO_3H$ |
| ΔdiHS-di(U,6)S | $SO_3$— | $COCH_3$ | $SO_3H$ |
| ΔdiHS-tri(U,6,N)S | $SO_3H$ | $SO_3H$ | $SO_3H$ |

Meanwhile, the structures indicated by the above-mentioned abbreviations may be represented as follows.

ΔdiHS-0S: ΔhexA1→4HexNAc, ΔdiHS-NS: ΔhexA1→4HexNS, ΔdiHS-6S: ΔhexA1→4HexNAc(6S), ΔdiHS-US: ΔhexA(2S) 1→4HexNAc, ΔdiHS-di(6,N)S: ΔhexA1→4HexNS(6S), ΔdiHS-di(U,N)S: ΔhexA(2S) 1→4HexNS, ΔdiHS-di(U,6)S: ΔhexA(2S) 1→4HexNAc (6S), ΔdiHS-tri(U,N,6)S: ΔhexA(2S) 1→4HexNS(6S)

In the above description, ΔhexA, HexNAc, and HexNS represent unsaturated uronic acid, N-acetylhexosamine, and N-sulfated hexosamine, respectively, and the numbers or alphabets shown in the parentheses represent a binding site of a sulfate group.

Test Method 1

[Disaccharide Analysis by Enzyme Digestion]

A method of analyzing a substitution site of a sulfate group in a sulfated polysaccharide was performed as follows. That is, each sulfated polysaccharide was enzymatically digested, and the resultant unsaturated disaccharide (the above-mentioned structural formula: Chemical formula 1) was analyzed by high performance liquid chromatography (HPLC) (see "2·8 Structural analysis using glycosaminoglyean degrading enzyme and HPLC in combination" described in Non-patent Document 2). The peak area of each unsaturated disaccharide was calculated, and the peak area with respect to the total area is represented as a percentage.

(1) Digestion of Oxidized Polysaccharide and Low-Molecular-Weight Sulfated Polysaccharide with Degrading Enzyme In accordance with the method described in Shin Seikagaku Jikken Koza 3, Carbohydrates II (published by Tokyo Kagaku Dojin Co., Ltd., 1991) p. 49-62, 1.0 mg of a sulfated polysaccharide or a low-molecular-weight sulfated polysaccharide was dissolved in 220 μl of 20 mM sodium acetate (pH 7.0) containing 2 mM calcium acetate, and then 20 mU of heparinase and 20 mU of heparitinase I and II were added thereto, followed by reaction at 37° C. for two hours.

(2) Analysis by HPLC

Sulfated polysaccharides and low-molecular-weight sulfated polysaccharides were digested with the degrading enzyme, and the resultant solutions (50 μl each) were analyzed by HPLC (IRIKA, model 852). Absorbance at 232 nm was determined using an ion-exchange column (Dionex Corporation, CarboPac PA-1 column 4.0 mm×250 mm). The determination was performed based on tetra- to dodecasaccharide standards (Yamada, et al., J. Biol. Chem., 270, 8696-8706, (1995)) in accordance with the method using a gradient system of lithium chloride (50 mM to 2.5 M) at a flow rate of 1 ml/min (Kariya, et al., Comp. Biochem. Physiol., 103B, 473, (1992)).

The results of disaccharide composition analysis of bovine kidney HS and mouse EHS-HS used in this test are shown in Table 3.

TABLE 3

| Disaccharide composition (%) | ΔdiHS-0S | ΔdiHS-NS | ΔdiHS-6S | ΔdiHS-US | ΔdiHS-di(6,N)S |
|---|---|---|---|---|---|
| Bovine kidney HS | 53 | 16 | 11 | 0.9 | 6.3 |
| Mouse EHS-HS | 33 | 58 | 0.3 | 0.5 | 1.5 |

| Disaccharide composition (%) | ΔdiHS-di(U,N)S | ΔdiHS-tri(U,6,N)S | ΔdiHS-HS-di(U,6)S | NS(total) |
|---|---|---|---|---|
| Bovine kidney HS | 7 | 5.8 | N.D | 35.1 |
| Mouse EHS-HS | 3.1 | N.D | N.D | — |

"NS(total)" represents a total of ΔDiHS-NS, ΔDiHS-(6,N)S, ΔDiHS-di(U,N)S, and ΔDiHS-tri(U,6,N)S.
In the above-mentioned table, "N.D" means below the detection limit.

In the above-mentioned table, "N.D" means below the detection limit.

Reference Example 4

Preparation of Streptavidin-Immobilized Plate

Streptavidin (manufactured by Vector Laboratories Inc.) was diluted with PBS(−) to 20 μg/ml, and the streptavidin solution was added to a MaxiSorp(registered trademark) 96-well microplate (manufactured by Nalge Nunc International K.K.) at 50 μl/well, and the plate was stored at 4° C. for 14 to 18 hours to coat the plate uniformly. The plate was washed with PBS(−) twice, and then phosphate buffer (PBS (−) containing no sodium chloride and no potassium chloride, pH 7.2 to 7.5: hereinafter, referred to as "PB") containing ApplieDuo (final dilution ratio: 5-fold, manufactured by Seikagaku Corporation) as a blocking substance for blocking a part uncoated with streptavidin and 0.05% ProClin(registered trademark) 300 (manufactured by SUPELCO) as an antiseptic was added thereto, and the plate was allowed to stand at room temperature for two hours. After that, the blocking solution was sufficiently removed, and the plate was dried at 37° C. for two hours, to thereby yield a desired streptavidin-immobilized plate. The plate was packed in an aluminum-laminated bag together with a desiccant, and stored in a refrigerator.

Reference Example 5

Preparation of Bi-Gag-Immobilized Plate

Bi-GAG prepared in Reference Example 2 was dissolved in PBS(−) containing ApplieDuo(registered trademark) (final dilution ratio: 20-fold, manufactured by Seikagaku Corporation) as an additive and 0.05% ProClin 300 as an antiseptic (hereinafter, referred to as "reaction solution A"), to thereby yield a 1 μg/ml solution. The streptavidin-immobilized plate prepared in Reference Example 4 was washed with 300 μl of PBS(−) containing 0.05% polyoxyethylene (20) sorbitan monolaurate (registered trademark, ICI, a product corresponding to Tween 20, available from Wako Pure Chemical Industries, Ltd.) and 0.05% Proclin(registered trademark) 300 as an antiseptic (hereinafter, referred to as "washing solution") four times, and then the Bi-GAG solution was added at 100 μL/well, and the plate was allowed to stand at room temperature for 30 minutes, to thereby bind Bi-GAG to the immobilized streptavidin (hereinafter, referred to as "Bi-GAG-immobilized plate).

Example 1

1. Preparation of NAH Antigen~Part 1

(1) Preparation of Reductively Aminated Nah (Hereinafter, Referred to as "RA-NAH")

NAH prepared in Reference Example 1 was weighed in an amount of 50 mg, and dissolved in 2 ml of an aqueous solution of 2 M ammonium chloride. 25 mg of sodium cyanoborohydrate was added to the solution, and a reductive amination reaction was carried out at 70° C. for two days. Then, 13 mg of sodium cyanoborohydrate was added to the reaction solution, and the reaction was performed under the same condition for two more days. The solution was cooled in an ice bath, and 400 μl of acetic acid was added to completely stop the reaction. RA-NAH was collected by the solvent precipitation method using double volume of ethanol and washed with ethanol, followed by freeze-drying, to thereby yield 39.5 mg of a freeze-dried product of RA-NAH.

(2) Preparation of 2-pyridyl Disulfide Propionylated NAH (hereinafter, referred to as "PDP-NAH")

RA-NAH prepared in the item (1) above was weighed in an amount of 10.4 mg, and dissolved in 2 ml of 0.1 M sodium chloride-0.1 M phosphate buffer (pH 7.5). 80 μl of a solution of 5 mM N-succinimidyl-3-(2-pyridyldithio)propionate (hereinafter, referred to as "SPDP", Sigma-Aldrich Co.) dissolved in ethanol was added thereto, and the PDP reaction was carried out at room temperature for 30 minutes. The solution was dialyzed against distilled water to remove excessive SPDP, followed by freeze-drying, to thereby yield 9.5 mg of a freeze-dried product of PDP-NAH.

(3) Preparation of Thiopropionyl NAH(SH-NAH)

PDP-NAH prepared in the item (2) above was weighed in an amount of 9.5 mg, and dissolved in 1 ml of 0.1 M sodium chloride-0.1 M sodium acetate buffer (pH 4.5). Dithiothreitol was added to the solution so as to achieve a final concentration of 25 mM to perform reduction reaction at room temperature for 60 minutes. SH-NAH was collected by the solvent precipitation method using double volume of ethanol. The resultant precipitate was washed with ethanol and freeze-dried, to thereby yield 8.3 mg of a freeze-dried product of SH-NAH.

(4) Preparation of 2-pyridyl Disulfide Propionylated Protein (PDP-Protein)

100 mg of BSA (manufactured by Sigma-Aldrich Co.) or 60 mg of KLH (manufactured by Sigma-Aldrich Co.) was dissolved in 0.1 M sodium chloride-0.1 M phosphate buffer (pH 7.5) so as to achieve a final concentration of 2.5 mg/ml. A solution of 5 mM SPDP dissolved in ethanol was added to the solution so as to achieve a final concentration of 238 μM, and the PDP reaction was carried out at room temperature for 30 minutes. The reaction solution was dialyzed against distilled water overnight to remove excessive SPDP, followed by freeze-drying, to thereby yield 104.2 mg of a freeze-dried product of PDP-BSA and 59.4 mg of a freeze-dried product of PDP-KLH.

(5) Preparation of NAH-Protein Conjugate Via Disulfide Bond (NAH-SS-KLH)

SH-NAH prepared in the item (3) above and PDP-BSA prepared in the item (4) above were used for requirement study of a GAG/protein mix ratio, and as a result, the GAG/protein mix ratio was determined as 2. Then, SH-NAH (1.5 mg) and PDP-KLH (0.75 mg) were dissolved in 1 ml of 0.1 M sodium chloride-0.1 M phosphate buffer (pH 7.5), and the conjugation reaction was performed at room temperature for two hours. The reaction solution was dialyzed against distilled water overnight to remove pyridyl-2-thione generated in the reaction solution, followed by freeze-drying, to thereby yield 1.9 mg of a freeze-dried product of NAH-SS-KLH. The resultant NAH-SS-KLH was used as an NAH antigen.

2. Preparation of NAH Antigen

Preparation of Protein Conjugate Via Carboxyl Group of NAH~part 2

10 mg/ml solutions of NAH prepared in Reference Example 1 and BSA (manufactured by Bayer Serological) were prepared with 0.1 M 2-morpholineethanesulfonic acid (hereinafter, referred to as "MES") buffer (pH 5.5). A 100 mg/ml solution of N-ethyl-N'-(3-dimethylaminopropyl)carbodiimide (hereinafter, referred to as "EDC", manufactured by Pierce Biotechnology) was prepared with 0.1 M MES buffer (pH 5.5). The NAH solution (300 μl) and BSA solution (150 μl) were mixed. To the mixed solution, there was added 4 μl of the EDC solution, and the conjugation reaction was performed at room temperature for 20 hours. The reaction solution was dialyzed against distilled water overnight and freeze-dried, to thereby yield 3.5 mg of a freeze-dried product of NAH-BSA.

Example 2

Production of Hybridoma which Produces Anti-NAH Monoclonal Antibodies (1) Immunization The NAH antigen prepared in "Preparation of NAH antigen~part 1" in Example 1 was dissolved in a small amount of purified water, and the resultant solution was added to TiterMAX Gold (2 ml, manufactured by Sigma-Aldrich Co.), which was used as an adjuvant, so as to achieve a final concentration of 0.5 mg/ml (antigen solution). The antigen solution was administered subcutaneously to four BALB/C mice (6-week-old female mice, Charles River Laboratories Japan, Inc.) in an amount of 100 μl/head twice or three times every two weeks. Then, final immunization was performed by administering only the antigen. Three days after the final immunization, the lymph node or spleen was removed, to thereby yield immunized lymphocytes.

(2) Production of Hybridoma

The lymphocytes obtained in the item (1) above and cultured mouse myeloma cells (P3U1, Shima Laboratories Co., Ltd.) were mixed at a rate of 4.4:1 to 5:1, and fused in the presence of 50% polyethyleneglycol 1500 (manufactured by Roche). The fused cells were cultivated in RPMI 1640 (manufactured by Kohjin Bio Co., Ltd) containing 15% fetal calf serum and HAT for about eight days until colonies were amplified. Cloning was performed using a generally used method, i.e., the limiting dilution method. The cells were diluted with the above-mentioned medium so that one or less cell was present in each well of a 96-well microplate, and cultivated. One or two microplates were used for one mouse, to yield a single clone. The cloning was repeated once or twice.

(3) Primary Screening of Antibodies by ELISA

From eight days after cell fusion, primary screening of antibodies was performed by the ELISA method. NAH-BSA prepared in "2. Preparation of NAH antigen~part2" in Example 1 or NAH-SS-KLH prepared in "1. Preparation of NAH antigen~part1" in Example 1 was added to a 96-well microplate at 1 μg/ml in an amount of 50 μl per well and immobilized. The antigen solution was discarded, and the plate was blocked with Block Ace (Dainippon Sumitomo Pharma Co., Ltd.) diluted 4-fold at room temperature for one hour or at 4° C. overnight. The blocking solution was discarded, and then the culture supernatant was added at 50 μl/well, followed by incubation at 37° C. for one hour. Subsequently, alkaline phosphatase-conjugated anti-mouse IgG+M+A (manufactured by Zymed Industries Inc.) diluted 1,000-fold with 10-fold diluted Block Ace was added at 50 μl/well, and the plate was incubated at 37° C. for one hour. The plate was washed with purified water four times, and a substrate solution (ALProse, manufactured by Shino-Test Corporation) was added at 50 μl/well, followed by incubation at room temperature for 20 minutes. In the same way as described above, a coloring solution was added to develop a color, and absorbance at 495 nm (control: 660 nm) was determined using a plate reader. Eight clones that exhibited strong colors were selected, and six clones of them that maintained their activities at the stage of culture in a 24-well plate were evaluated by secondary screening.

(4) Secondary Screening of Antibodies by ELISA Method

The six clones selected in the item (3) above were evaluated by secondary screening, i.e., by the ELISA method using biotin-labeled NAH (hereinafter referred to as "Bi-NAH").

The Bi-NAH-immobilized plate produced in Reference Example 5 was washed with the washing solution four times, and a culture supernatant was added to the plate at 100 μl/well. The plate was allowed to stand at room temperature (15 to 25° C.) for 60 minutes to perform an antigen-antibody reaction. A well containing only the reaction solution was used as a blank. After completion of the reaction, the plate was washed with the washing solution four times, and a secondary antibody solution obtained by diluting horseradish peroxidase-labeled goat anti-mouse immunoglobulin antibody (manufactured by Dako) 2,000-fold with the reaction solution was added at 100 μl/well. The plate was allowed to react at room temperature for 60 minutes to perform antigen-antibody reaction. After completion of the reaction, the plate was washed with the washing solution four times, and a tetramethylbenzidine solution (hereinafter, referred to as "TMB solution", manufactured by BioFX Laboratories) was added as a substrate for peroxidase at 100 μl/well, followed by the reaction at room temperature for 30 minutes to develop color. A reaction stop solution (manufactured by BioFX Laboratories) was added to the plate at 100 μl/well to stop the reaction, and absorbance at a wavelength of 450 nm (reference wavelength: 630 nm), which was increased by decomposition of TMB (see Example 4), was determined using a well reader SK-603(registered trademark) (purchased from Seikagaku Corporation). The reactivity of each antibody was evaluated based on the absorbance difference calculated by subtracting the absorbance of the blank from the absorbance of a culture supernatant of each clone for Bi-NAH (hereinafter, referred to as absorbance difference).

As described above, immunization was performed with the NAH antigen, followed by hybridoma selection and cloning, to thereby establish three clones capable of producing antibodies against NAH (clone names: NAH33, NAH43, and NAH46).

Purification of Monoclonal Antibody (1) Collection of Ascitic Fluid

Three pristane-treated BALB/C mice (15-week-old female mice, provided by Charles River Laboratories Japan, Inc.) were used to prepare ascitic fluids containing the clones. To the abdominal cavity of each mouse were transplanted $5\times10^6$ cells, and the ascitic fluid was collected from the tenth day to the twelfth day several times. The volumes of the ascitic fluids containing the three clones (NAH33, NAH43, and NAH46) were 20 ml, 26 ml, and 40 ml, respectively. The antibody contents in the collected ascitic fluids were evaluated by the cellulose acetate membrane electrophoresis (nitrocellulose membrane (SERECA-V), 60 mM barbital buffer (pH 8.6), 1 mV/cm (width), nigrosine staining).

(2) Purification of Antibodies

The isotypes of the antibodies were examined in accordance with a conventional method, and the isotype of all the three antibodies was found to be IgM κ-chain. Therefore, the antibodies were purified by chromatography using HiTrap IgY Purification HP column (5 ml, Amersham Bioscience). Specifically, the mouse ascitic fluid was dialyzed against a binding buffer (20 mM phosphate buffer, 0.5 M $K_2SO_4$, pH 7.5), followed by filtration using a 0.45 μm filter. The filtrate was passed through the column sufficiently equilibrated with a binding buffer. The column was washed with the binding buffer until the monitored OD value reached zero, and then an elution buffer (20 mM phosphate buffer, pH 7.5) was passed through the column to elute proteins bound to the column. The eluted protein fractions were collected, and ammonium sulfate powder was added so as to achieve 50% saturation to precipitate proteins. The precipitates were collected by centrifugation, and the resultant product was sufficiently dialyzed against PBS. The protein content was determined, and a purity test was performed (A280, the concentration was converted as 1%=13.0, purity test by cellulose acetate membrane electrophoresis). As a result, purified antibodies, NAH33 antibody, NAH43 antibody, and NAH46 antibody, were obtained in amounts of 3.4 mg, 0.4 mg, and 3.1 mg, respectively.

Example 4

Characteristics of the Purified Monoclonal Antibodies

Method

The reactivity of NAH33 antibody, NAH43 antibody, and NAH46 antibody to various antigens was examined by the ELISA method using Bi-GAG-immobilized plates.

The Bi-GAG-immobilized plates produced in Reference Example 5 were washed with the washing solution four times, and then solutions containing the respective test antibodies, which were diluted with the reaction solution A so as to achieve a desired concentration (hereinafter, referred to as "test antibody solutions"), were added at 100 μl/well. The plate was allowed to stand at room temperature for 60 minutes to perform an antigen-antibody reaction. A well containing only the reaction solution A was used as a blank. After completion of the reaction, the plate was washed with the washing solution four times, and a secondary antibody solution prepared by diluting horseradish peroxidase-labeled goat anti-mouse immunoglobulin antibody (manufactured by Dako) 2,000-fold with the reaction solution A was added at 100 μl/well. The plate was allowed to stand at room temperature for 60 minutes to perform the antigen-antibody reaction. After completion of the reaction, the plate was washed with the washing solution four times, a tetramethylbenzidine solution (hereinafter, referred to as "TMB solution", manufactured by BioFX Laboratories) was added as a substrate for peroxidase at 100 μl/well, followed by the reaction at room temperature for 30 minutes to develop color. A reaction stop solution (manufactured by BioFX Laboratories) was added to the plate at 100 μl/well to stop the reaction, and absorbance at a wavelength of 450 nm (reference wavelength: 630 nm), which was increased by decomposition of TMB, was determined using the well reader SK-603(registered trademark) (purchased from Seikagaku Corporation). The reactivity of each antibody was evaluated based on the absorbance difference calculated by subtracting the absorbance in the case of using a blank (reaction solution A) instead of the test antibody solution from the absorbance in the case where each test antibody solution was allowed to react with Bi-GAG (hereinafter, referred to as absorbance difference). When not specified, the concentrations of the three antibodies, i.e., NAH33 antibody, NAH43 antibody, and NAH46 antibody, in the test antibody solutions were 0.3 μg/ml, 0.8 μg/ml, and 0.04 μg/ml, respectively, which were given by the previous study on optimal concentrations of the antibodies with regard to the reactivity to Bi-NAH. However, in the test on modified GAGs described in FIG. 4, the concentrations of NAH33 antibody, NAH43 antibody, and NAH46 antibody were 0.2 μg/ml, 0.5 μg/ml, and 0.02 μg/ml, respectively.

Results

1. Reactivity to Various Biotin-Labeled GAGs (Bi-GAGs)

Figure 2:
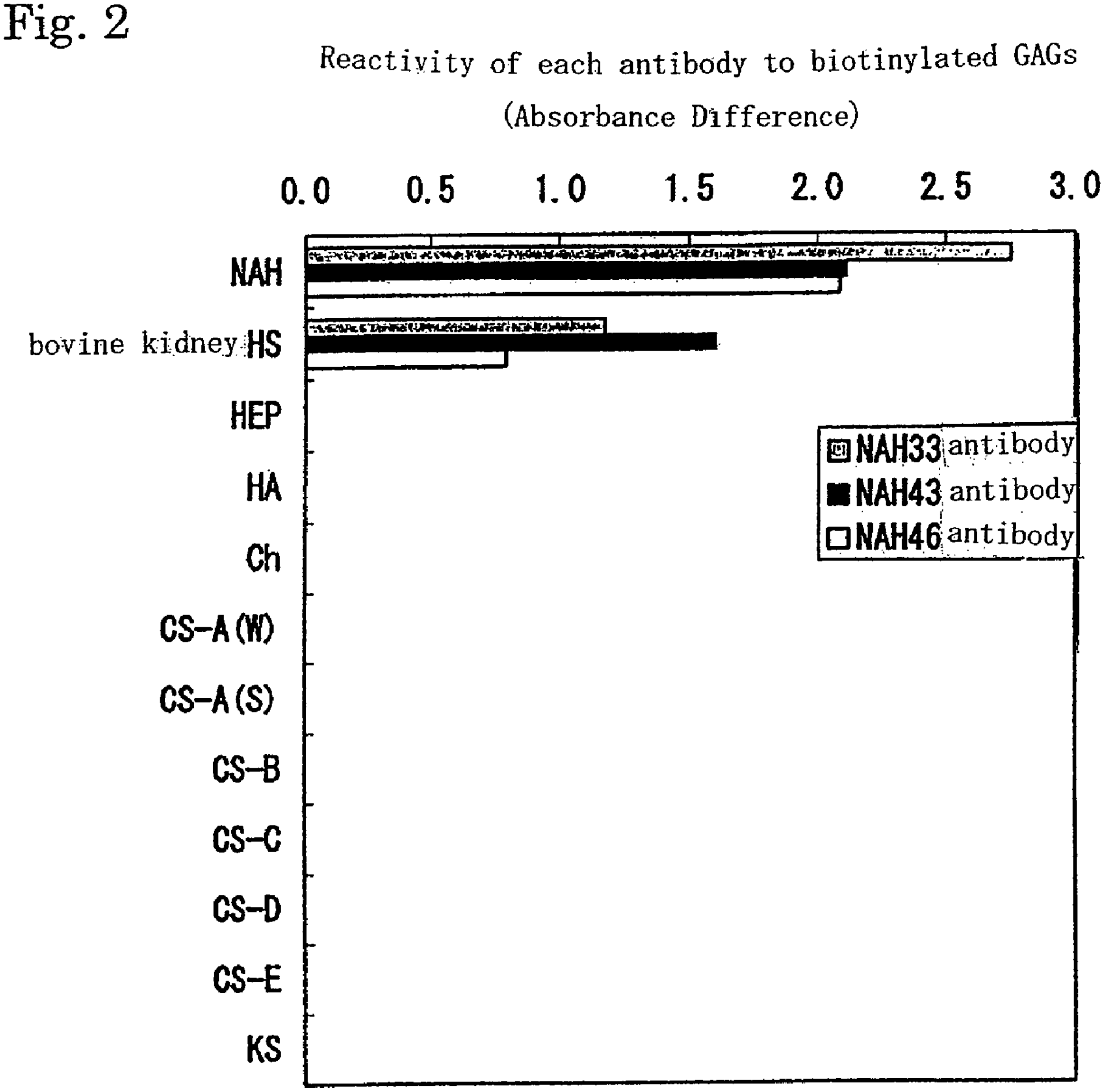
FIG. 2 A first diagram showing the reactivity of NAH33 antibody, NAH43 antibody, and NAH46 antibody to GAGs.

The reactivity of the three antibodies to various GAGs (NAH, bovine kidney HS, HA, HEP, Ch, CS-A(S), CS-A(W), CS-B, CS-C, CS-D, CS-E, and KS) was determined by the above-mentioned method to examine the specificities. The results of the reactivity of the antibodies to various GAGs are shown in FIG. 2. The reactivity of the antibodies was evaluated based on absorbance differences (FIG. 2).

All of NAH33 antibody, NAH43 antibody, and NAH46 antibody were found to have reactivity to Bi-NAH and Bi-HS and have no reactivity to Bi-HA, Bi-HEP, Bi-Ch, Bi-CS-A (S), Bi-CS-A(W), Bi-CS-B, Bi-CS-C, Bi-CS-D, Bi-CS-E, and Bi-KS.

2. Reactivity to NAH Analogue and Modified NAH

Figure 3:
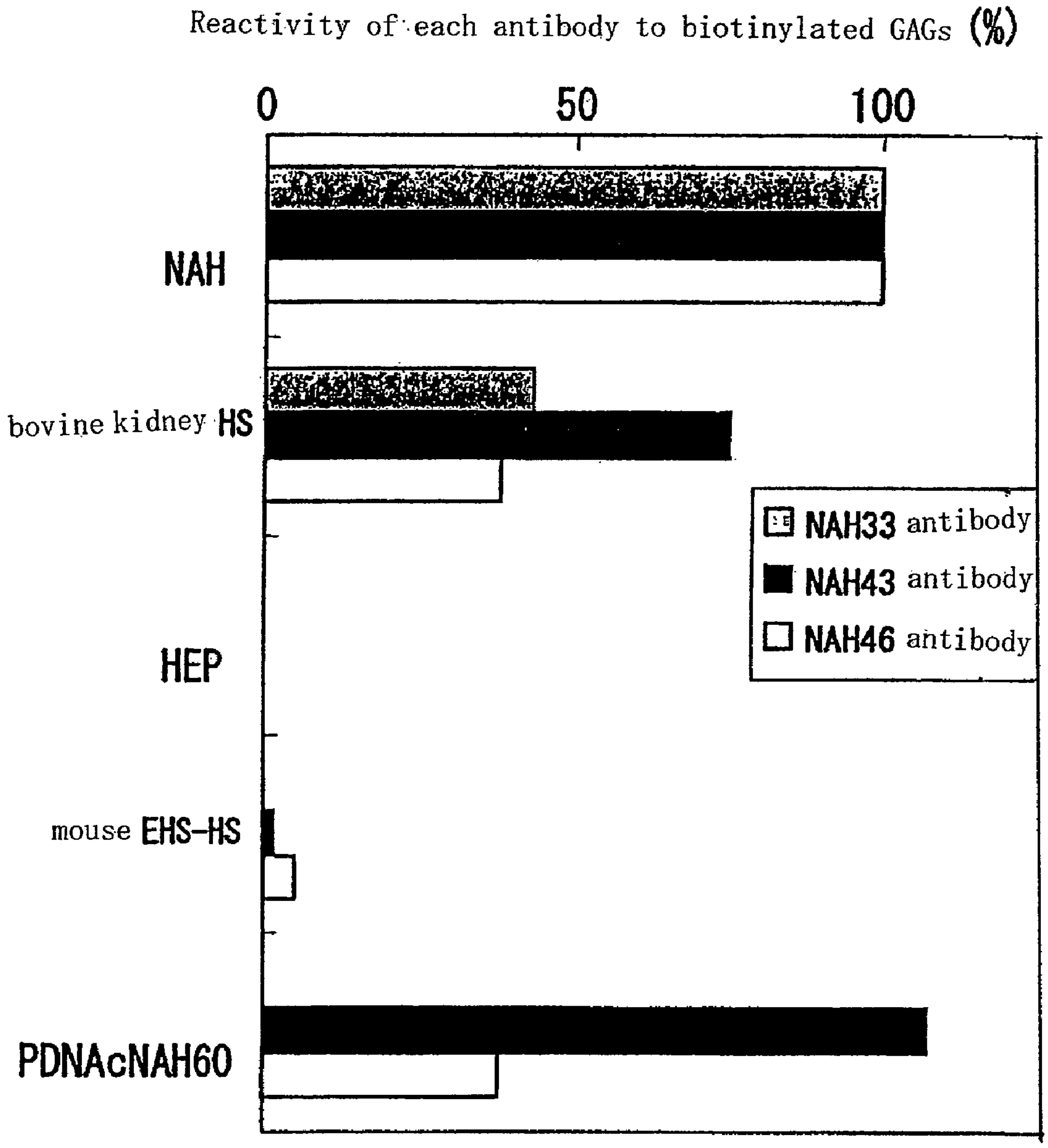
FIG. 3 A second diagram showing the reactivity of NAH33 antibody, NAH43 antibody, and NAH46 antibody to GAGs.

To examine recognition sites of the three antibodies in more detail, the reactivity of the antibodies was examined using an NAH analogue and a modified NAH (FIG. 3). Mouse EHS-HS prepared by the method described in JP 07-53756 B was used as the NAH analogue. Mouse EHS-HS is a molecule having the same basic skeleton as HS and including D-glucosamine residues in which about 65% of its N-positions are sulfated.

Figure 4:
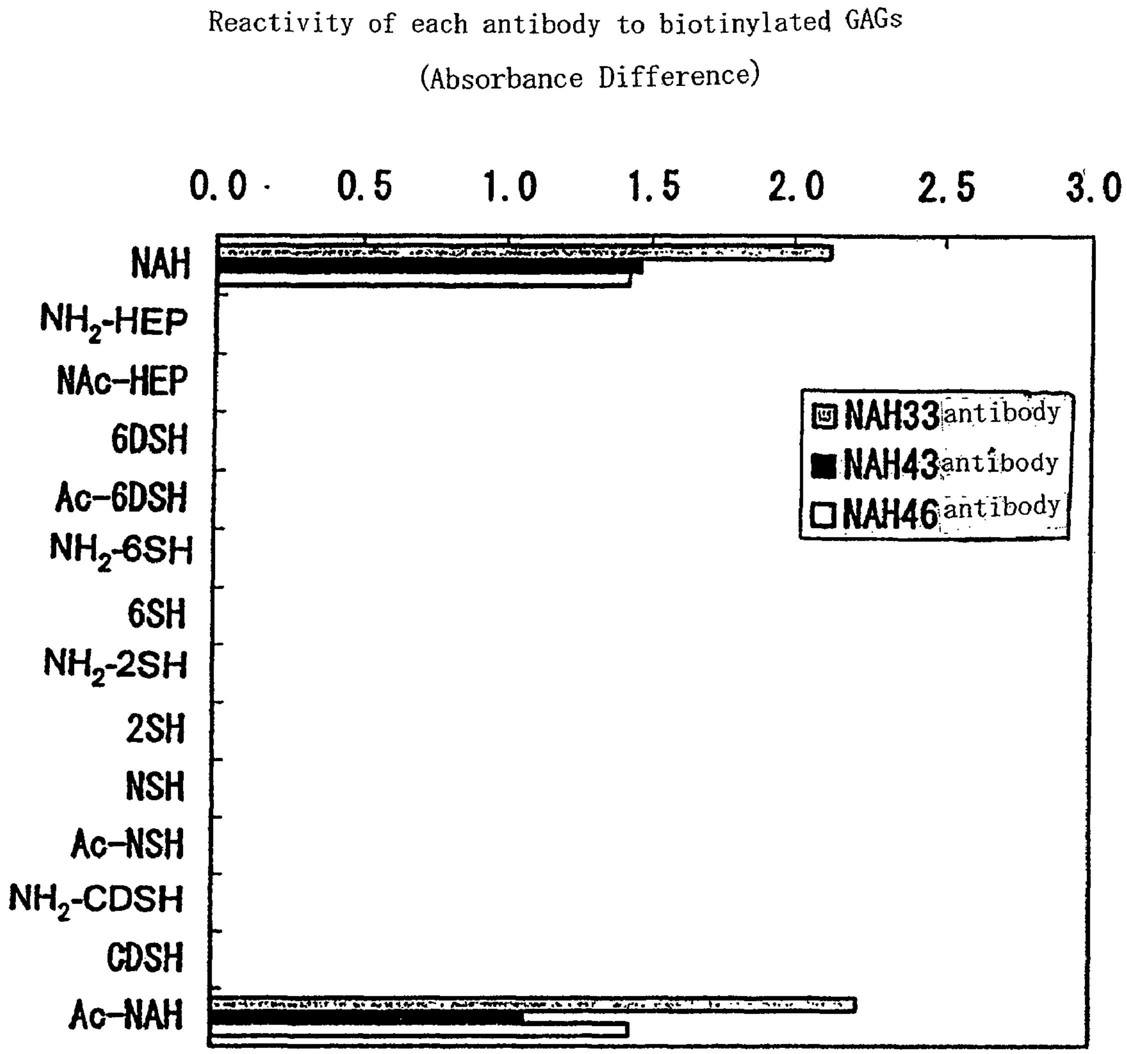
FIG. 4 A third diagram showing the reactivity of NAH33 antibody, NAH43 antibody, and NAH46 antibody to GAGs.

Meanwhile, the above-mentioned PDNAc-NAH60 was used as a modified NAH. The reactivity of each antibody was evaluated as a relative value, i.e., the reactivity to biotin-labeled EHS-HS (Bi-EHS-HS) or Bi-PDNAc-NAH60 prepared in accordance with the method described in Reference Example 2 with respect to the reactivity to Bi-NAH (absorbance difference) defined as 100%. Determination was performed by the same method as described in "1. Reactivity to various biotin-labeled GAGs (Bi-GAGs)" above. A test on the reactivity to a site-specifically desulfated product obtained from HEP as a starting material, described in "2. Biotin labeling of chemically-modified GAG" in Reference Example 2, and to N-acetylated NAH (Ac-NAH) was performed by the same method as described above (FIG. 4). FIG. 4 does not show relative values calculated based on the reactivity of NAH but shows absorbance difference.

NAH33 antibody reacted with NAH and bovine kidney HS but did not react with EHS-HS and PDNAc-NAH60. This result suggests that acetylated amino groups in a glucosamine residue are important in the reaction of NAH33 antibody to NAH or HS, and glucosamine or N-sulfated glucosamine may act negatively to inhibit the reaction. The facts suggest that an antigen determinant in the reaction of NAH33 antibody to NAH or HS includes GlcNAc, and its structure is important for the reaction.

NAH43 antibody reacted with NAH, bovine kidney HS, and PDNAc-NAH60, and the reactivity strength was found to be as follows: PDNAc-NAH60≧NAH>bovine kidney HS. On the other hand, the reactivity to mouse EHS-HS was found to be less than 2% as compared to that to NAH. The results suggest that, in the reaction of NAH43 antibody to NAH or HS, acetylation of amino acids in a glucosamine residue is not always important, but N-sulfated glucosamine may act negatively to inhibit the reaction. The facts suggest that an antigen determinant in the reaction of NAH43 antibody to NAH or HS includes GlcNAc and $GlcNH_2$.

NAH46 antibody reacted with NAH, bovine kidney HS, and PDNAc-NAH60, and the reactivity strength was found to be as follows: NAH>bovine kidney HS=PDNAc-NAH60. On the other hand, the reactivity to mouse EHS-HS was found to be about 5% as compared to that to NAH. The results suggest that acetylation of amino acids in a glucosamine residue is important in the reaction of NAH 46 antibody to NAH or HS, and glucosamine or N-sulfated glucosamine may act negatively to inhibit the reaction. The facts suggest that an antigen determinant in the reaction of NAH46 antibody to NAH or HS includes GlcNAc, and its structure is important for the reaction.

3. Confirmation of the Specificity of Each Antibody

Figure 5A:
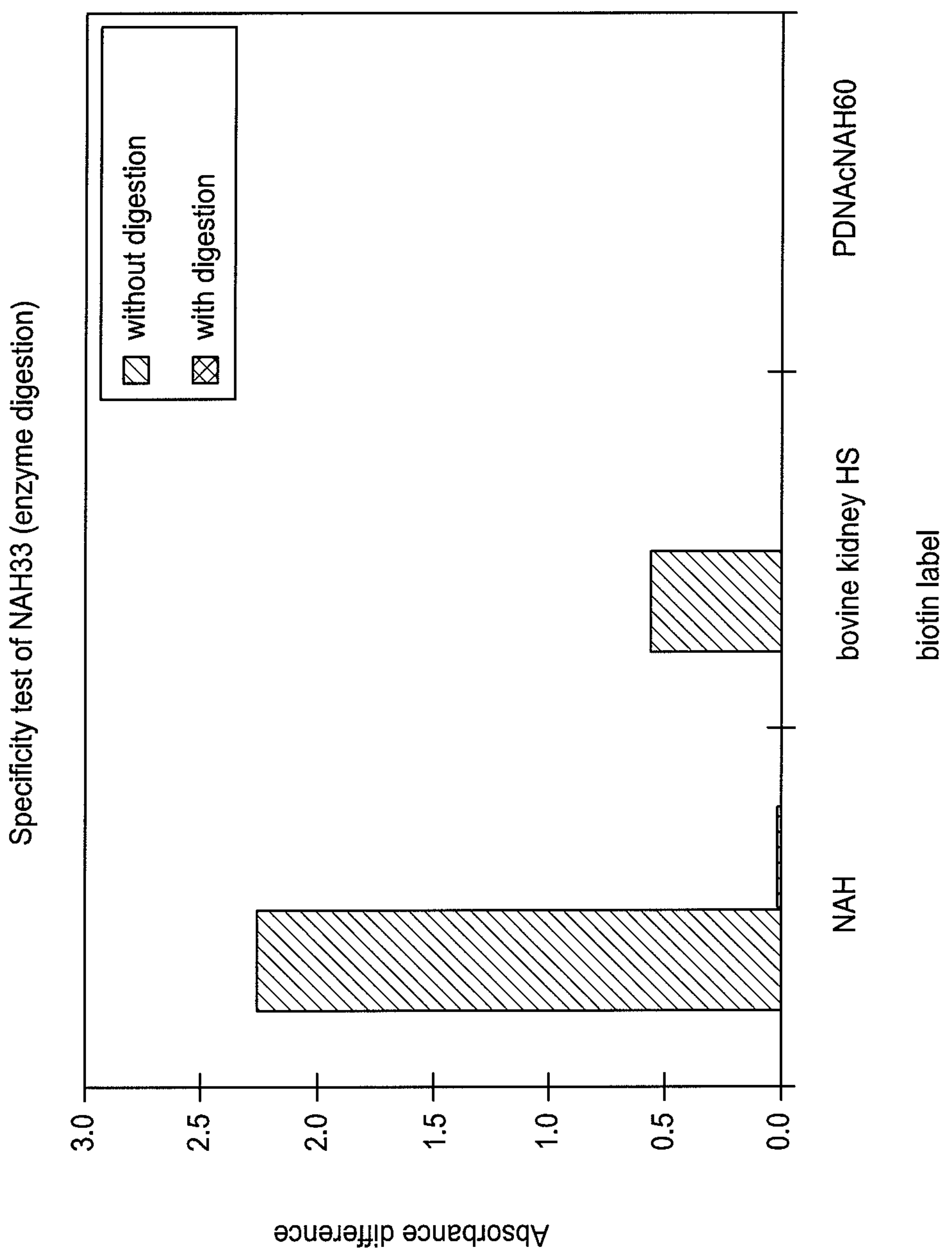
FIG. 5 Diagrams showing specific the reactivity of NAH33 antibody (A), NAH43 antibody (B), and NAH46 antibody (C).
Figure 5B:
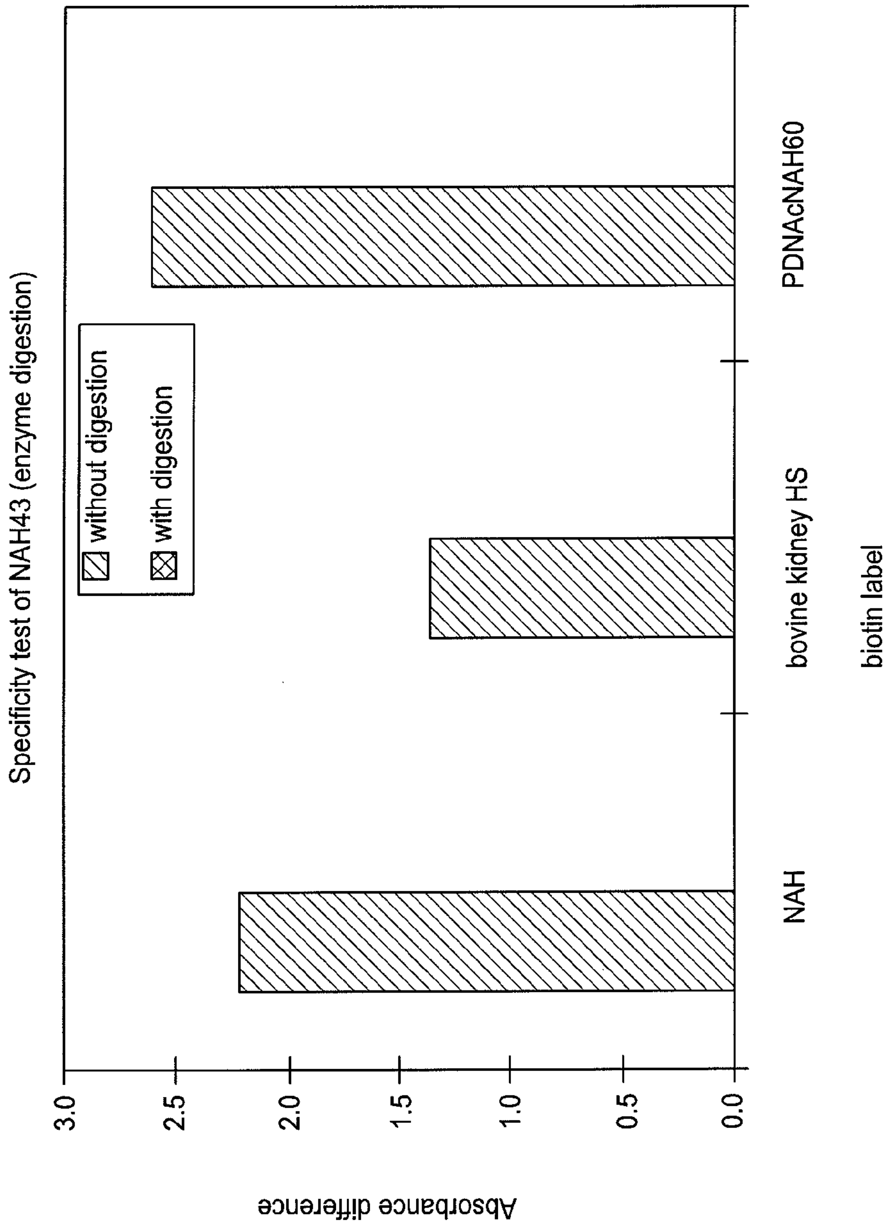
Figure 5C:
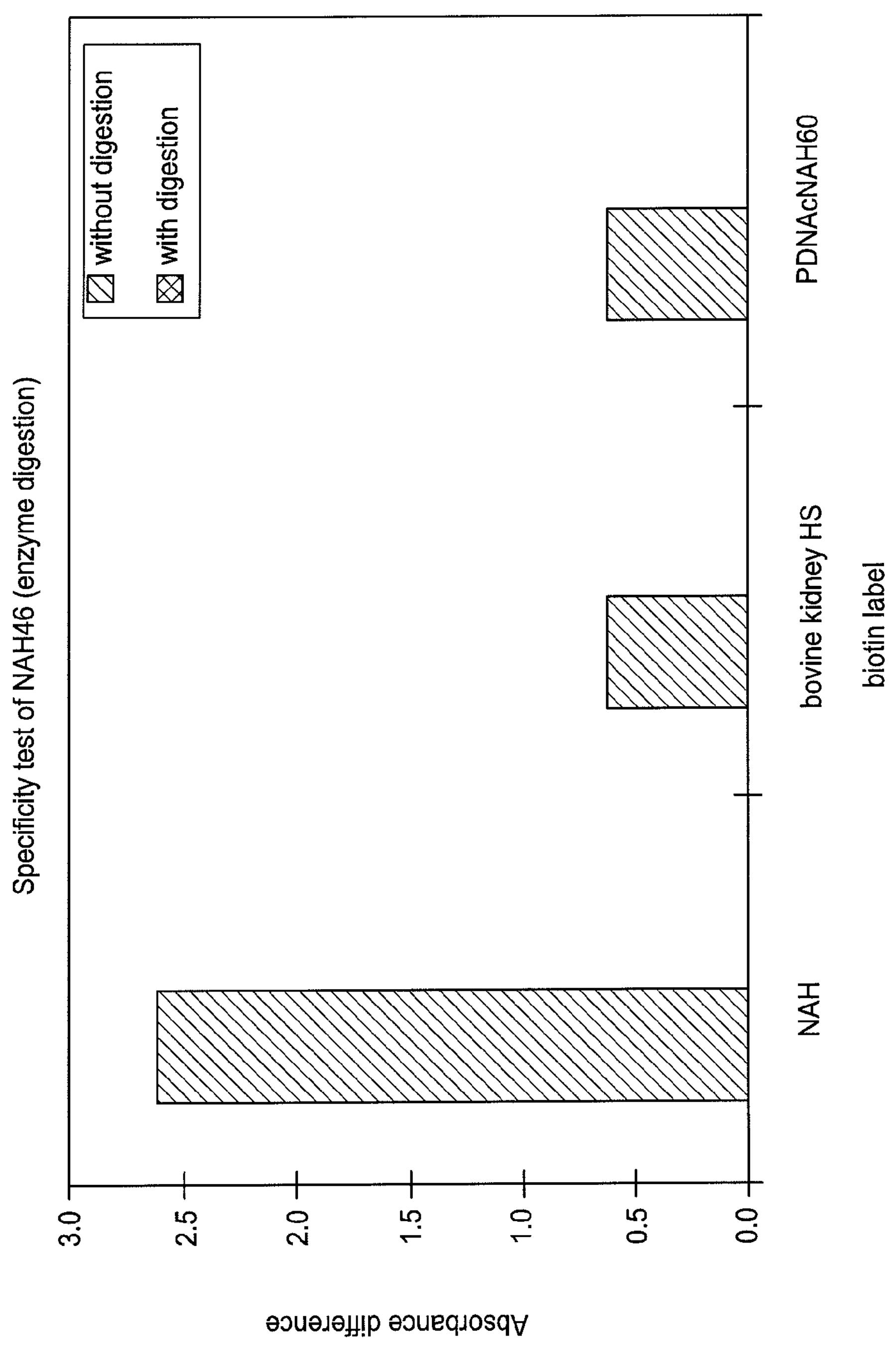
Figure 6A:
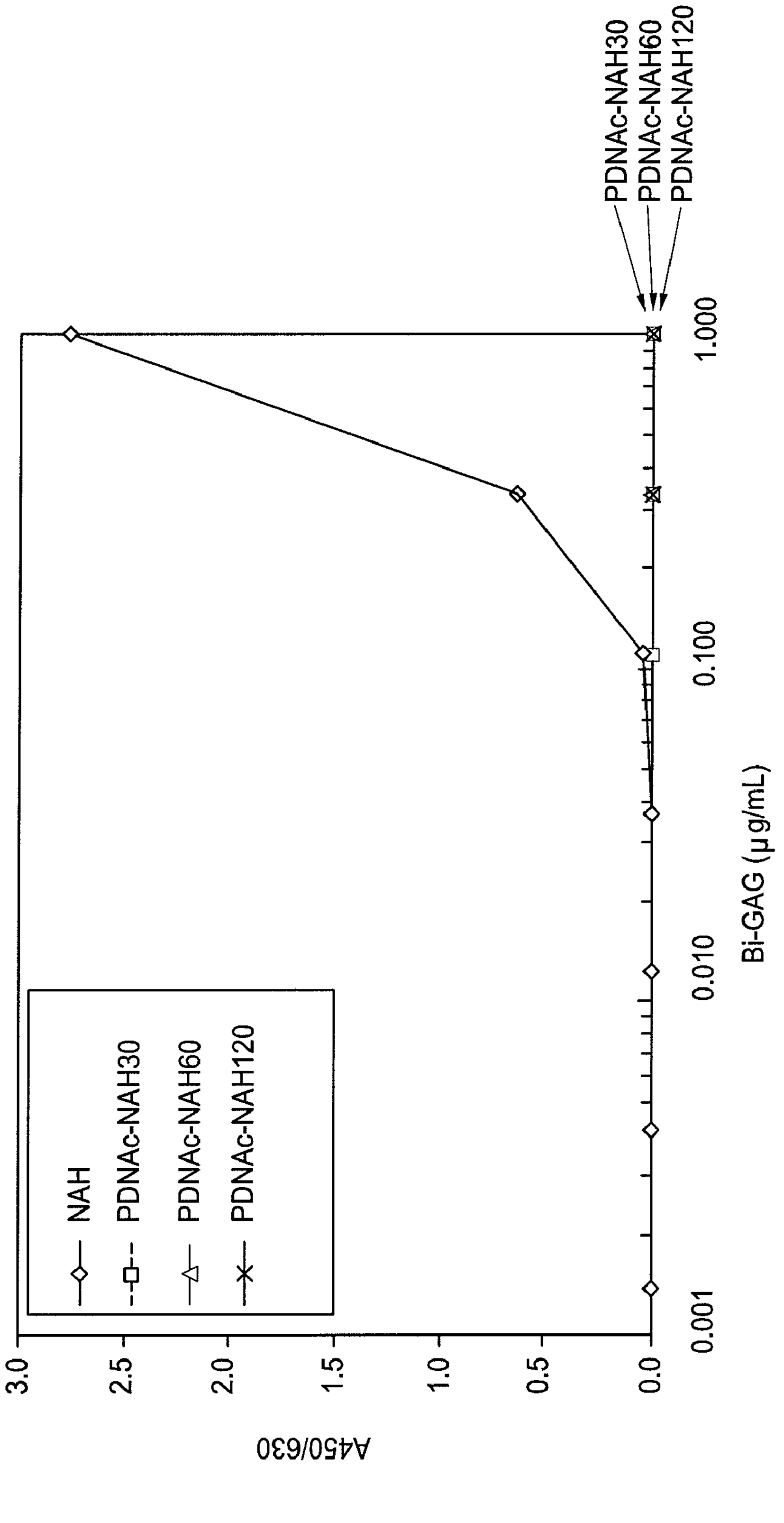
FIG. 6 First diagrams showing the reactivity of NAH33 antibody, NAH43 antibody, and NAH46 antibody against different concentrations of Bi-GAGs. The graphs (a) and (b) represent the reactivity of NAH33 antibody, the graphs (c) and (d) represent the reactivity of NAH43 antibody, and the graphs (e) and (f) represent the reactivity of NAH46 antibody.
Figure 6B:
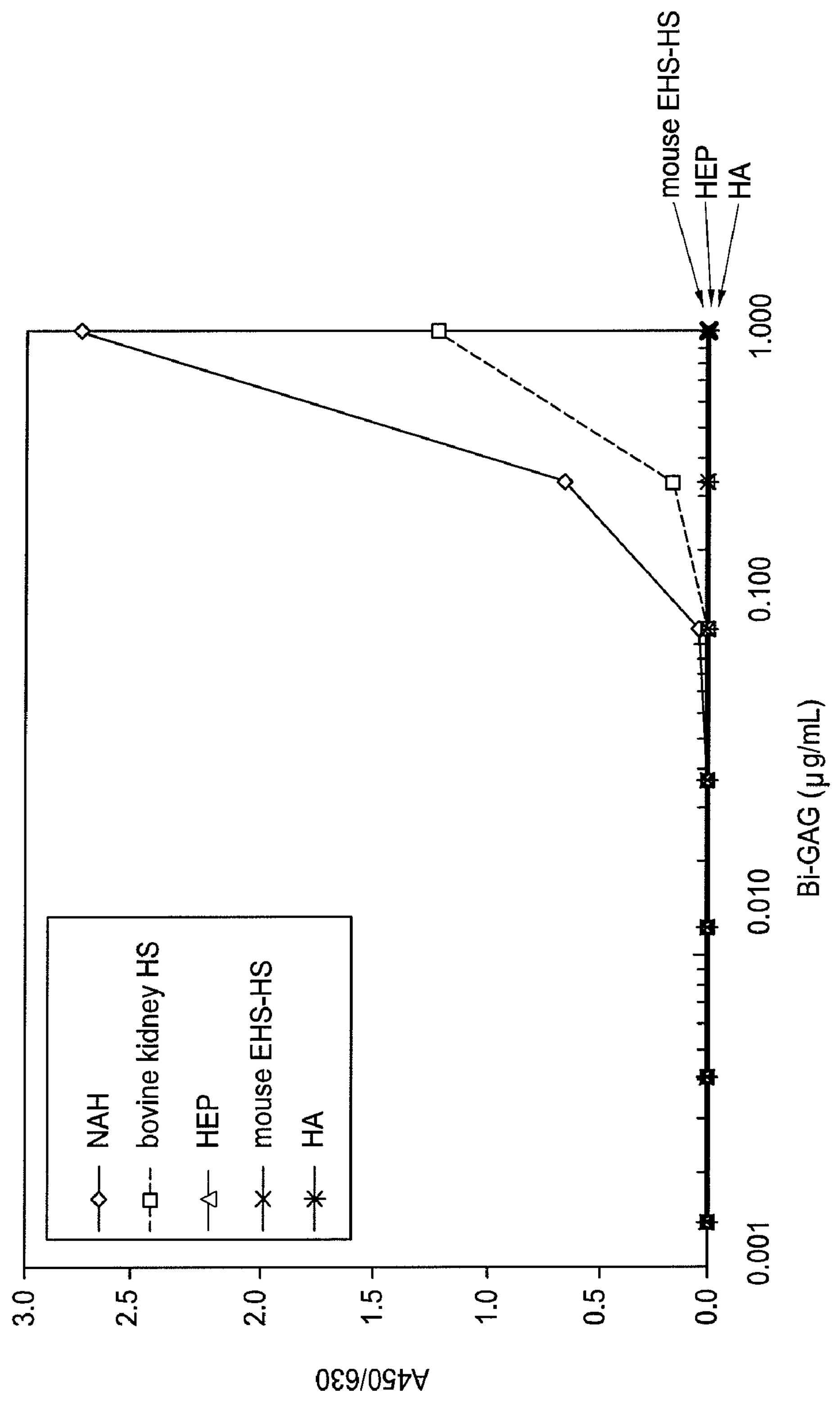
Figure 6C:
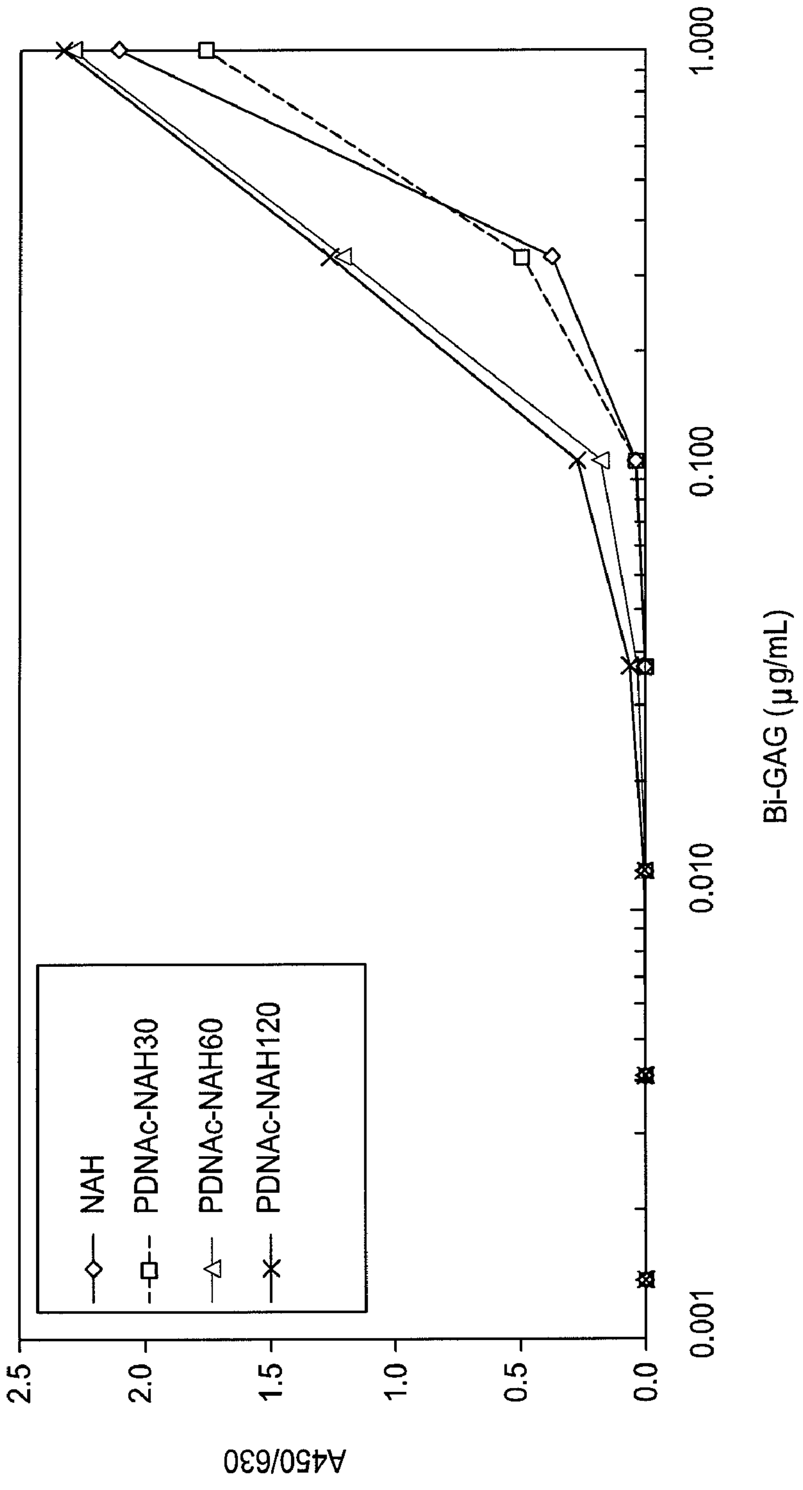
Figure 6D:
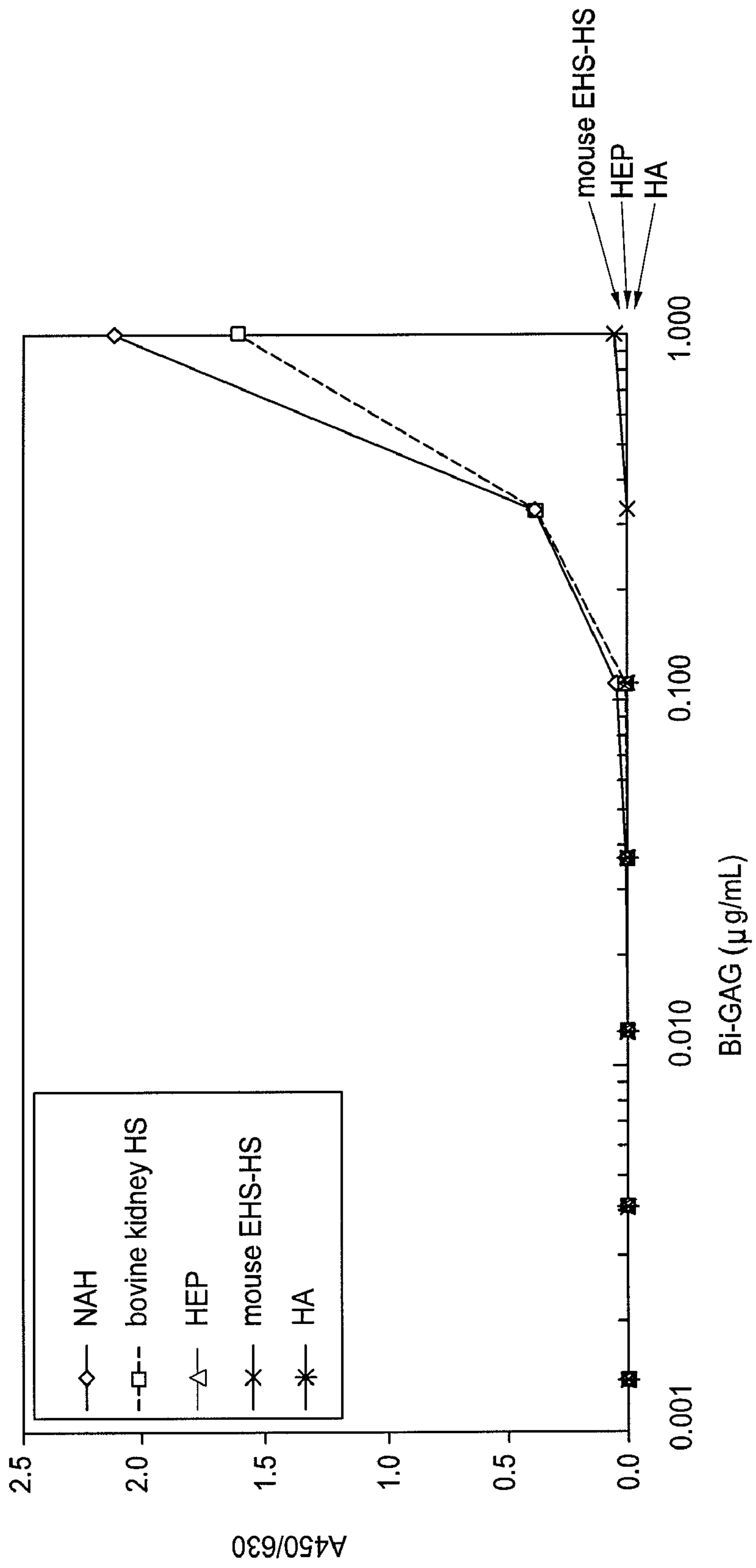
Figure 6E:
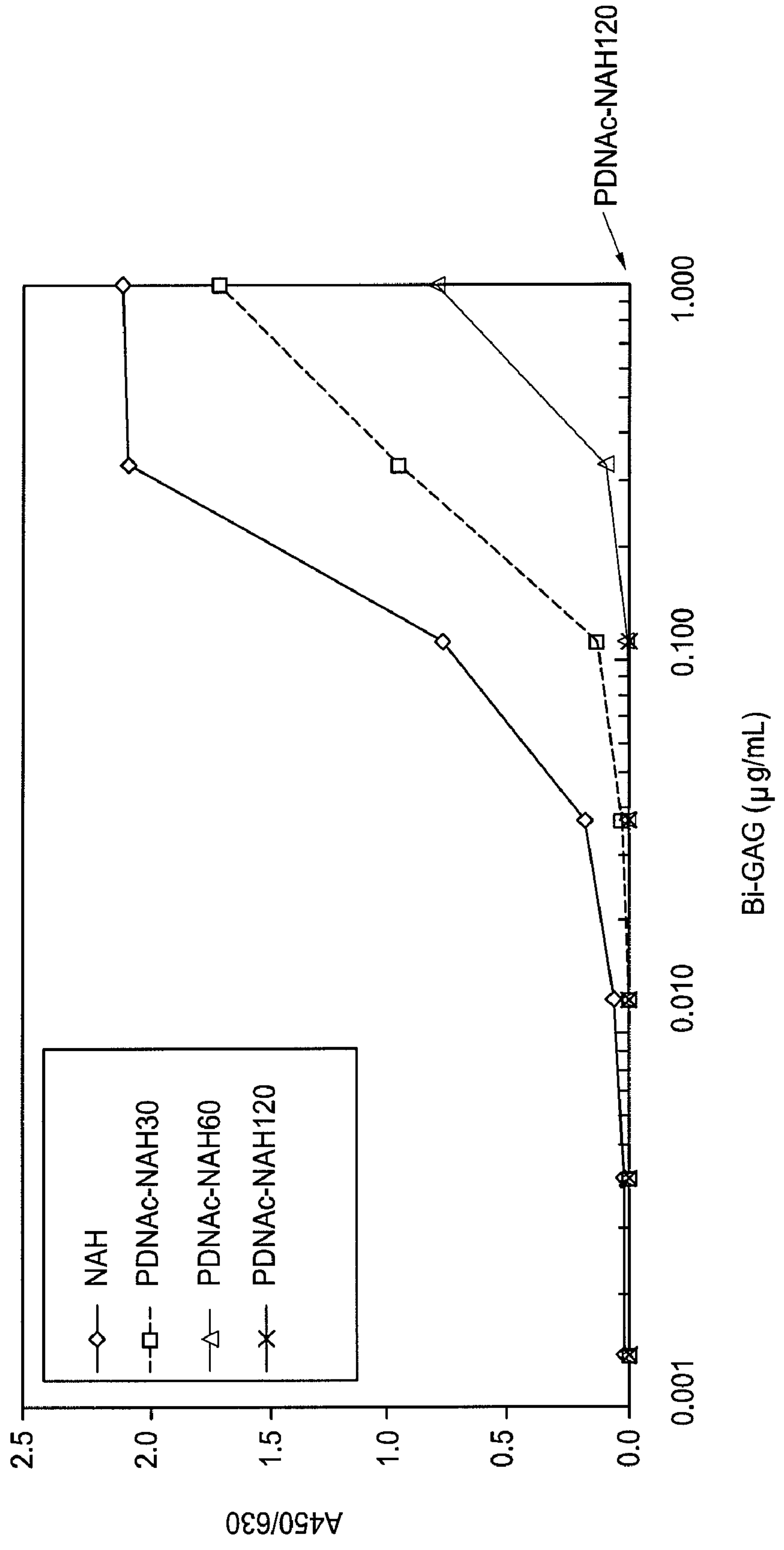
Figure 6F:
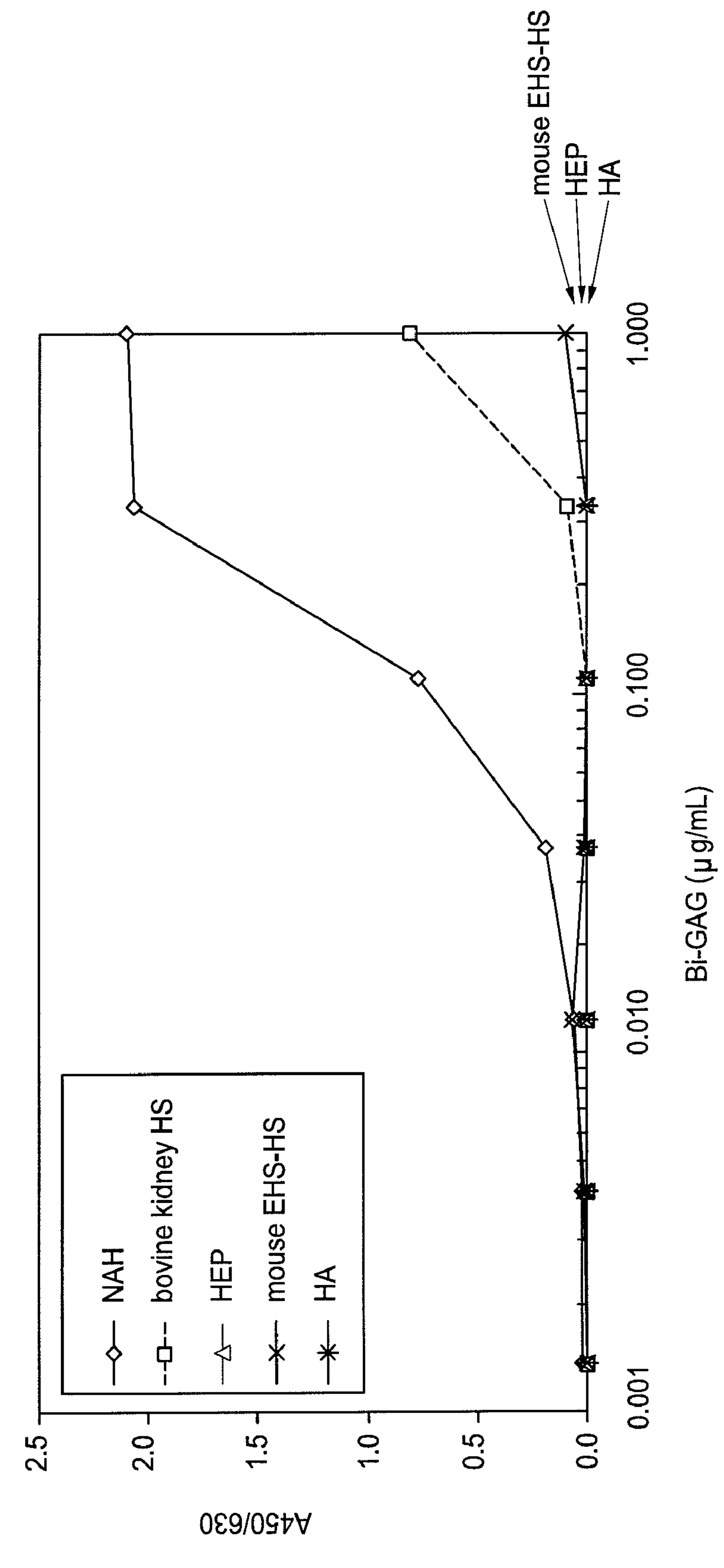

To confirm reaction specificities of the three kinds of antibodies, Bi-NAH, Bi-HS, Bi-PDNAc-NAH60 were decomposed with heparitinase (manufacture by Seikagaku Corporation) to examine the decrease in or disappearance of the reactivity of the antibodies. Heparitinase solution was prepared to 50 mU/mL with 50 mM Tris (manufactured by Sigma-Aldrich Co.)-HCl buffer (pH 7.3 to 7.7) containing ApplieDuo® (final dilution ratio: 20-fold, manufactured by Seikagaku Corporation), 0.15 M sodium chloride (manufactured by Nacalai Tesque, Inc.), 5 mM calcium chloride (manufactured by Wako Pure Chemical Industries, Ltd.), and 0.05% ProClin 300 as an antiseptic (hereinafter, referred to as "diluted heparitinase solution"). The Bi-GAG-immobilized plate and Bi-PDNAc-NAH60-immobilized plate produced as the aforementioned examples were washed with the washing solution four times, and the diluted heparitinase solution was added at 100 μL/well. The plates were allowed to stand at 37° C. for two hours to digest immobilized Bi-GAG and immobilized Bi-PDNAc-NAH60. After digestion, the plates were washed in the same way as described above, and the three kinds of antibodies were added in accordance with the method described in the above-described example. Then, subsequent procedures were performed to determine the reactivity. The reactivity was evaluated based on absorbance difference. The results are shown in FIGS. 5(A) to (C).

Most of the reactivity of the three kinds of antibodies to both Bi-GAG and Bi-PDNAc-NAH60 disappeared due to heparitinase digestion. The results confirmed that the three kinds of antibodies specifically react with the GAGs and modified GAGs.

Example 5

Reactivity in the Case of Changing the Concentration of Bi-GAG

Figure 7:
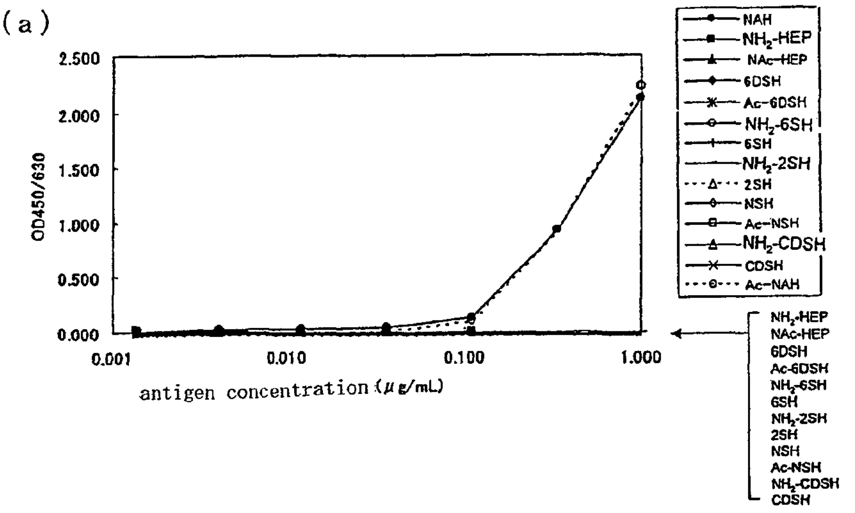
FIG. 7 Second diagrams showing the reactivity of NAH33 antibody, NAH43 antibody, and NAH46 antibody against different concentrations of Bi-GAGs. The graph (a) represents the reactivity of NAH33 antibody, the graph (b) represents the reactivity of NAH43 antibody, and the graph (c) represents the reactivity of NAH46 antibody.
Figure 7:
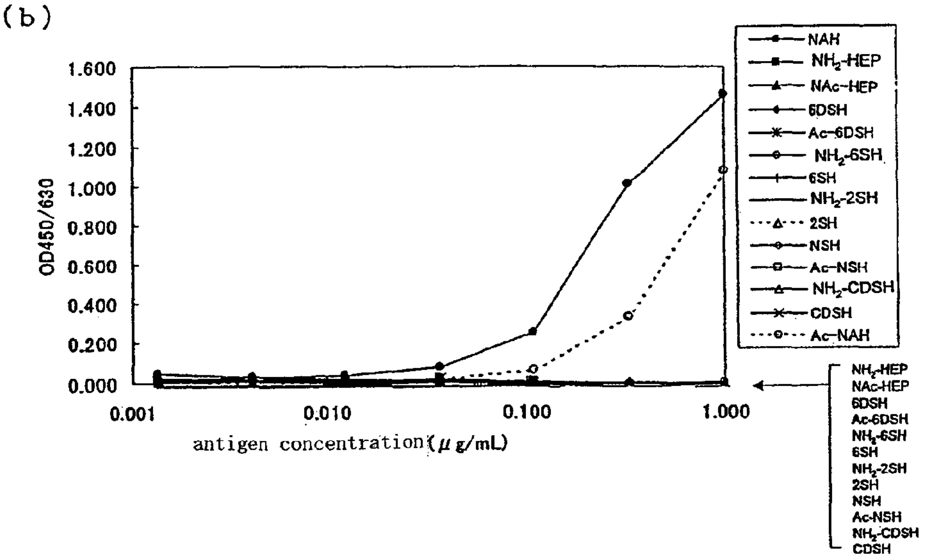
Figure 7:
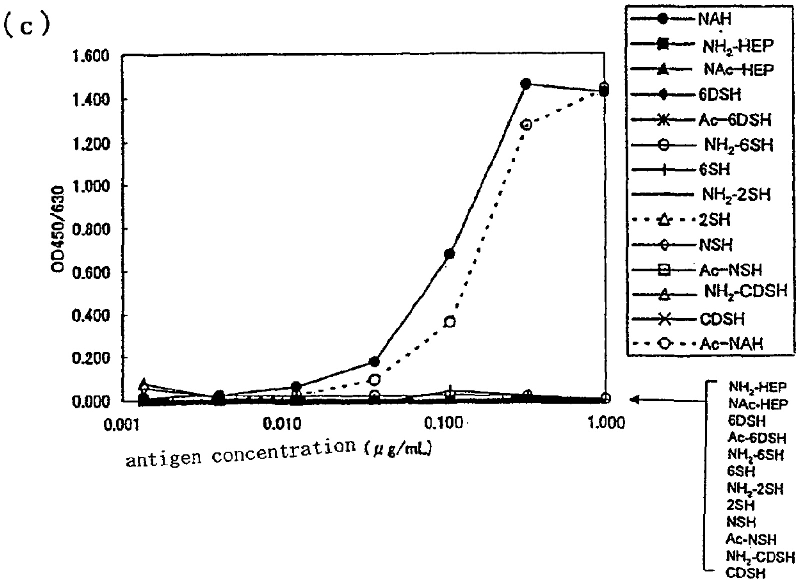

The reactivity of each antibody was analyzed by the same method as Example 4 except that the concentrations of Bi-GAGs were changed within the range of 0.0 to 1.0 μg/mL. In this example, PDNAc-NAH30, PDNAc-NAH60, PDNAc-NAH120, described in Reference Example 1, were used as the Bi-PDNAc-NAHs. The results are shown in FIGS. 6(*a*) to (*f*). In addition, the results for the GAGs, described in "2. Biotin labeling of chemically-modified GAG", are shown in FIGS. 7(*a*) to (*c*).

Example 6

(1) Immunohistochemical staining was performed using frozen sections of rat kidney to examine stainability. An SD rat (Charles River Laboratories Japan, Inc., 8-week-old male rat) was anesthetized with diethyl ether (manufactured by Wako Pure Chemical Industries, Ltd.) and killed by exsanguination from the aorta in the abdominal aorta, and the kidney was removed. The removed kidney was embedded in OCT compound (manufactured by Sankyo Miles) and frozen with acetone-dry ice, and sections with a thickness of 6 μm were created in a cryostat (purchased by Leica Microsystems).

The resultant sections were air-dried for two hours at room temperature and fixed with cold acetone (4° C.), followed by air-drying at room temperature for one hour. After that, the sections were washed with PBS(−) and immersed in distilled water containing 0.1% sodium azide (manufactured by Wako Pure Chemical Industries, Ltd.) and 0.3% hydrogen peroxide solution (manufactured by Wako Pure Chemical Industries, Ltd.) at room temperature for 10 minutes to remove endogenous peroxidase activity, and then the sections were washed with PBS(−) and blocked with PBS(−) containing 0.1% casein (manufactured by Wako Pure Chemical Industries, Ltd.) (hereinafter, referred to as "PBS") at room temperature for 60 minutes.

Then, the sections were washed with PBS(−), and endogenous biotin was blocked using avidin-biotin blocking kit (manufactured by Vector Laboratories Inc.).

After that, the sections were washed with PBS(−), and NAH33 antibody, NAH43 antibody, and NAH46 antibody were diluted with PBS to 0.5 μg/mL, 2 μg/mL, and 0.5 μg/mL, respectively, and were allowed to react at 4° C. overnight. The sections were washed with PBS(−), and biotin-labeled anti-mouse IgG+IgM containing 10% rat serum (manufactured by The Jackson Laboratories) was diluted 500-fold with PBS, followed by reaction at room temperature for 30 minutes. The sections were washed with PBS(−), and peroxidase-labeled streptavidin (manufactured by Nichirei Corporation) was allowed to react therewith at room temperature for 30 minutes. The sections were washed with PBS(−), and brown color development reaction was performed using DAB color development kit (manufactured by Zymed Laboratories Inc.).

After color development, the sections were immersed in PBS(−) to stop the reaction, and were washed with water for five minutes. After that, nuclear staining (blue) was performed with hematoxylin (manufactured by DAKO) for comparative staining. The sections were washed with water for five minutes, and dehydration and penetration procedures were performed in accordance with a conventional method, followed by embedding.

Figure 8:
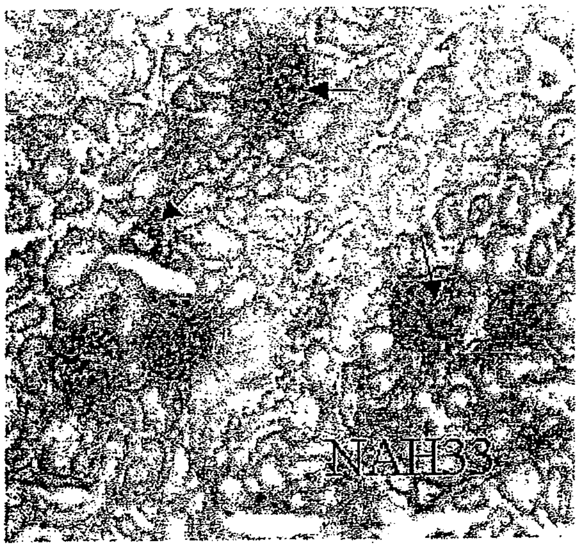
FIG. 8 Diagrams (photographs) showing the results of immunohistochemical staining of rat kidney frozen sections using NAH33 antibody (A), NAH43 antibody (B), and NAH46 antibody (C). The arrows show positive sites.
Figure 8:
Figure 8:
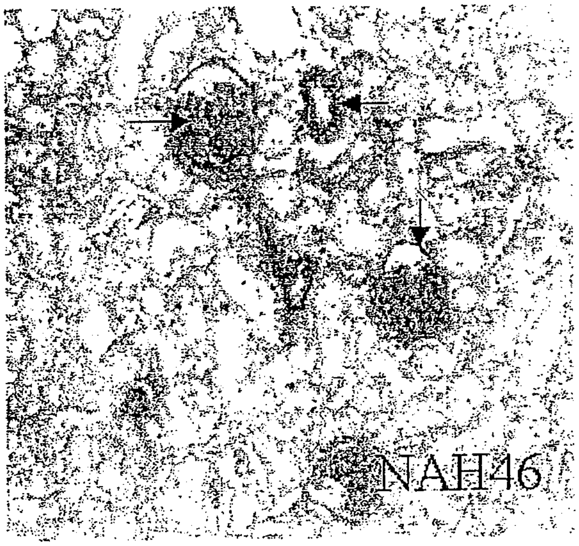

Staining images are shown in FIG. 8. In the cases of NAH 33 antibody and NAH46 antibody, brown strong positive reactions (arrowed lines) were observed in the renal glomerular basement membrane, vascular endothelium, and Bowman's capsule, while in the case of NAH43, positive reactions (arrowhead) were observed in the renal glomerular basement membrane and vascular endothelium.

(2) Confirmation of the Specificity by Heparitinase Digestion

Sections were prepared by the above-mentioned method, and were fixed with cold acetone (4° C.), followed by air-drying. The sections were washed with PBS(−), and heparitinase I (manufactured by Seikagaku Corporation) was diluted to 250 mU/ml with 20 mM acetic acid (manufactured by Wako Pure Chemical Industries, Ltd.) buffer (pH 7.0) containing 1 μM calcium acetate (manufactured by Wako Pure Chemical Industries, Ltd.) (hereinafter, referred to as "buffer") and allowed to react at 37° C. for two hours. As a control, only the buffer was allowed to react in the same way as described above. The sections were washed with PBS(−), and the antibodies were allowed to react in the same way as described above, followed by the brown color development reaction using the DAB color development kit (manufactured by Zymed Laboratories Inc.).

After color development, the sections were immersed in PBS(−) to stop the reaction, and washed with water for five minutes. After that, nuclear staining (blue) was performed with hematoxylin (manufactured by DAKO) for comparative staining. The sections were washed with water for five minutes, and dehydration and penetration procedures were performed in accordance with a conventional method, followed by embedding.

Figure 9:
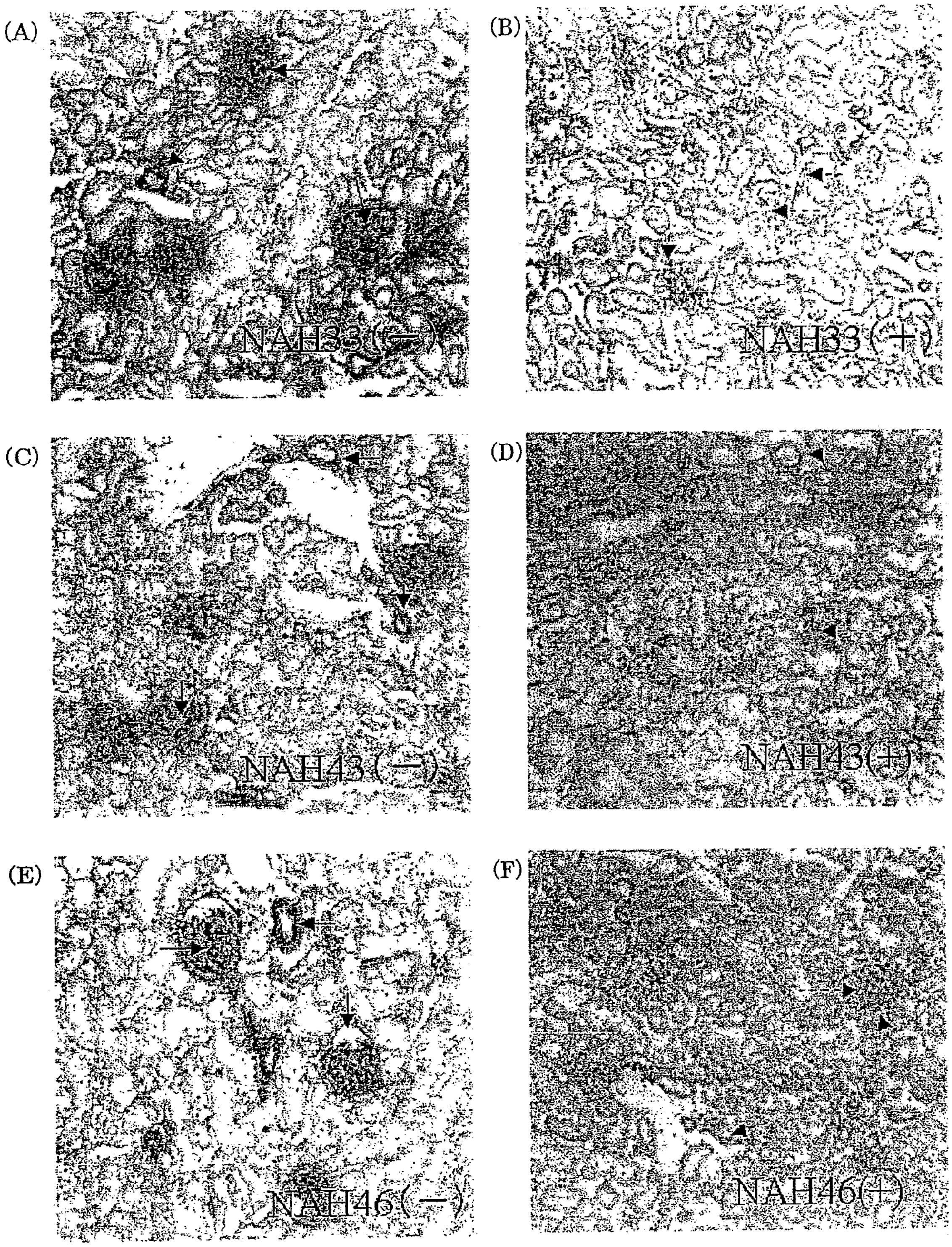
FIG. 9 Diagrams (photographs) showing the results of immunohistochemical staining in the case of heparitinase digestion treatment (B, D, and F) and in the case of no heparitinase digestion treatment (A, C, and E). The photographs A and B show the results of staining using NAH33 antibody, the photographs C and D show the results of staining using NAH43 antibody, and the photographs E and F show the results of staining using NAH46 antibody. The solid line arrows represent positive sites. The dashed line arrows represent sites where positive reactions disappeared.

Staining images are shown in FIG. 9. As compared with the control, in the case of the sections digested with heparitinase, the disappearance or reduction of the positive reactions (brown) were observed, and thus the antibodies were found to specifically recognize HS.

Example 7

Detection of Bovine Kidney HS Using Antigen-Immobilized Plate

One of the antigens of the present invention, NAH46 antibody, was used to detect bovine kidney HS using an antigen-immobilized plate.

1. Method (1) Preparation of Antibody-Immobilized Plate

NAH46 antibody was diluted to 20 μg/ml with PBS(−), and the antibody solution was added to a MaxiSorp (registered trademark) 96-well microplate at 50 μl/well, and the plate was stored at 4° C. for 14 to 18 hours to coat the plate uniformly. The plate was washed with PBS(−) twice, and phosphate buffer (PBS(−) containing no sodium chloride and no potassium chloride, pH 7.2 to 7.5) containing ApplieDuo (final dilution ratio: 5-fold) as a blocking substance and 0.05% ProClin (registered trademark) 300 as an antiseptic was added thereto, and the plate was allowed to stand at room temperature for two hours. After that, the blocking solution was sufficiently removed, and the plate was dried at 37° C. for two hours, to thereby yield a desired NAH46 antibody-immobilized plate. The NAH46 antibody-immobilized plate was packed in an aluminum-laminated bag together with a desiccant, and stored in a refrigerator.

The same procedures were repeated except that JM403 and 10E4 (both manufactured by Seikagaku Corporation) were used instead of NAH46 antibody, to thereby prepare a JM403-immobilized plate and a 10E4-immobilized plate.

(2) Preparation of HRP-Labeled Antibody

The NAH46 antibody solution (1 mg/ml) was labeled with HRP using a commercially available HRP labeling kit (manufactured by Dojindo Laboratories) by a designated method. The resultant HRP-labeled antibody was diluted 800-fold with a solution containing ApplieDuo (final dilution ratio: 20-fold), pH 7.3 to 7.7 Tris-HCl (50 mM), NaCl (8 g/L), Tween 20 (0.05%), and ProClin 300 (0.05%) as an antiseptic (hereinafter, referred to as "reaction solution for measurement"), to thereby prepare an HRP-labeled antibody solution.

The same procedures were repeated except that JM403 and 10E4 were used instead of NAH46 antibody, to thereby prepare HRP-labeled antibody solutions of JM403 and 10E4, respectively.

(3) Detection of Bovine Kidney HS

The reaction solution for measurement was added to the antibody-immobilized plates described in the item (1) above at 100 μl/well. Subsequently, solutions of bovine kidney HS, prepared to about 10.0, 5.0, 2.5, 1.25, 0.63, 0.31, 0.16 μg/ml with the reaction solution for measurement, were added at 20 μl/well, and the plates were allowed to stand at 4° C. for 18 hours, to thereby form complexes of "immobilized antibody-bovine kidney HS" (first reaction). A well containing only the reaction solution for measurement (bovine kidney HS; 0 μg/ml) was used as a blank. After the first reaction, the plates were washed four times with a washing solution (a solution containing pH 7.3 to 7.7 Tris-HCl (50 mM), NaCl (8 g/L), Tween 20 (0.05%), and ProClin 300 (0.05%)) at 300 μl/well. After washing, the HRP-labeled antibody solutions prepared in the item (2) above were added at 100 μl/well in the combinations as shown in Table 4 below, and the plates were allowed to stand at 4° C. for three hours, to thereby form complexes of "immobilized antibody-bovine kidney HS-HRP-labeled antibody" (second reaction).

TABLE 4

| | Immobilized antibody | HRP-labeled antibody |
|---|---|---|
| (i) | NAH46 antibody | NAH46 antibody |
| (ii) | | JM403 |
| (iii) | | 10E4 |
| (iv) | JM403 | NAH46 antibody |
| (v) | 10E4 | NAH46 antibody |

The wells were washed by the same method as described above, and the TMB solution was added as a substrate for peroxidase at 100 μl/well for detection of HRP in the above complexes. The plates were allowed to stand at room temperature (15 to 25° C.) for 30 minutes to develop color. Subsequently, a reaction stop solution (manufactured by BioFX Laboratories) was added at 100 μl/well to stop the reaction, and absorbance at a wavelength of 450 nm, i.e., at the absorption wavelength of a product obtained by decomposition of TMB (reference wavelength: 630 nm), was determined using the well reader SK-603. Detection of bovine kidney HS was evaluated based on absorbance difference calculated by subtracting a blank absorbance.

2. Results

Figure 10:
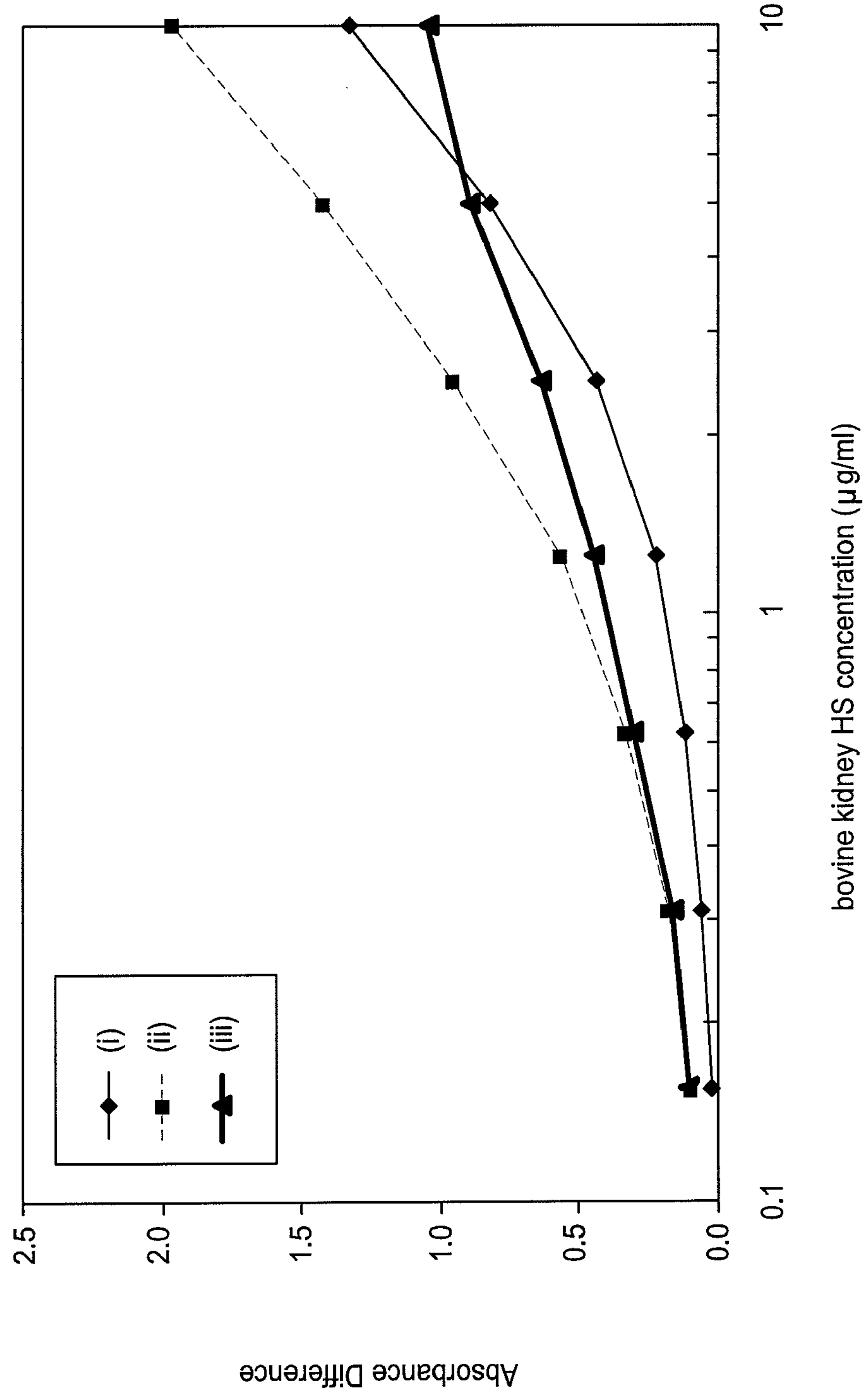
FIG. 10 A first diagram showing the detection of bovine kidney HS using antibody-immobilized plates ((i), (ii), and (iii) represent the combinations of the immobilized antibodies and HRP-labeled antibodies shown in Table 4.)
Figure 11:
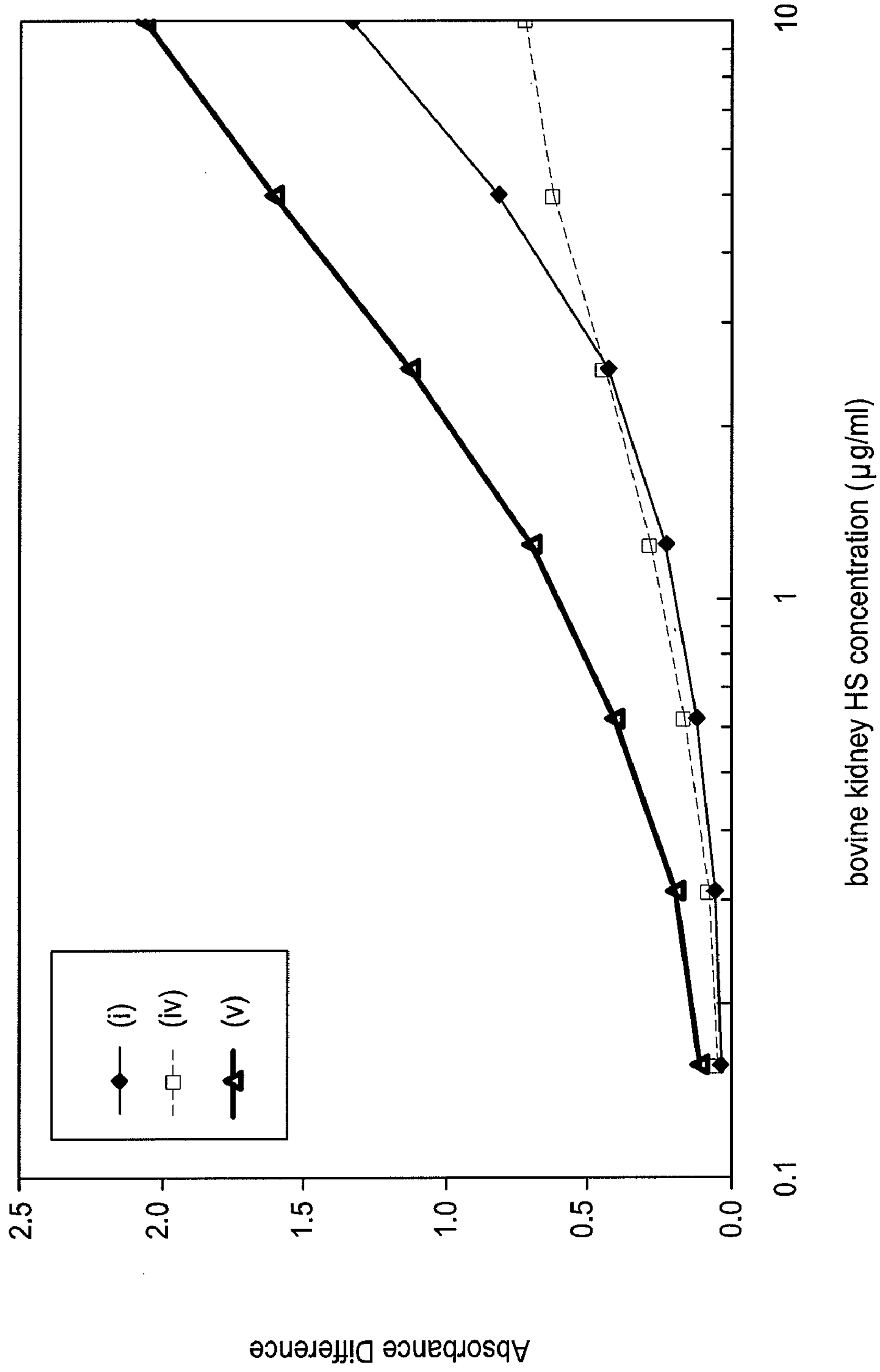
FIG. 11 A second diagram showing the detection of bovine kidney HS using antibody-immobilized plates ((i), (iv), and (v) represent the combinations of immobilized antibodies and HRP-labeled antibodies shown in Table 4.)

The results shown in FIGS. 10 and 11 revealed that, both in the case of using NAH46 antibody as an immobilized antibody and using NAH46 antibody, JM403, or 10E4 as an HRP-labeled antibody, and in the case of using NAH46 antibody as an HRP-labeled antibody and using JM403 or 10E4 as an immobilized antibody, bovine kidney HS could be detected, and the reactivity was found to be concentration-dependent.

Example 8

Detection of Hs on Cell Surface by Flow Cytometry

One of the antibodies of the present invention, NAH46 antibody, was used to detect HS on a cell surface by the flow cytometry method (hereinafter, referred to as FCM).

1. Method (1) Preparation of Cell colo201 cells (derived from human colon cancer, purchased from Dainippon Sumitomo Pharma Co., Ltd.) were suspended in a medium, and cultivated in a $CO_2$ incubator (manufactured by Ikemoto Scientific Technology Co., Ltd., in the presence of 5% $CO_2$, 37° C.) for three days. The medium was prepared by adding to RPMI 1640 with L-glutamine (manufactured by Sigma-Aldrich Co.) the heat-inactivated fetal calf serum (manufactured by ICN Biomedicals, Inc.) at a concentration of 10% and penicillin-streptomycin (Dainippon Sumitomo Pharma Co., Ltd.) so that the concentration of penicillin G sodium is 60 IU/mL and the concentration of streptomycin sulfate is 60 μg/mL. The resultant cultivated cells were suspended in PBS(−) to $10^6$ cells/mL. An aliquot of the suspension was taken and suspended in PBS(−) containing 50 mU/ml heparitinase I (manufactured by Seikagaku Corporation) and allowed to react under shading at 37° C. for 20 minutes, and cells with digested HS on their cell surfaces were defined as HS-negative cells. Cultivated cells treated with PBS(−) containing no heparitinase I in the same way as described above were defined as HS-positive cells.

(2) FCM

The HS-positive cells and HS-negative cells obtained in the section (1) above were separately subjected to washing by centrifugation (1,500 rpm, 5 minutes, 4° C.) with PBS(−) twice and suspended in a solution of 10 μg/mL of NAH46 antibody, followed by reaction under shading at 4° C. for 30 minutes. The resultant cells were subjected to washing by centrifugation twice and allowed to react with FITC-labeled anti-mouse IgG+IgM (manufactured by The Jackson Laboratories) diluted 50-fold with PBS(−) under shading at 4° C. for 30 minutes. The resultant cells were further subjected to washing by centrifugation twice and suspended in 1 mL of PBS(−), and the suspension was filtered using a tube equipped with a filter (manufactured by Becton, Dickinson and Company). The resultant cell suspensions were analyzed using a flow cytometer EPICS XL-MCL (manufactured by Beckman Coulter, Inc.).

The same treatments and analyses were performed except that mouse IgM (manufactured by Sigma-Aldrich Co.) was used instead of the NAH46 antibody, and the results were defined as a negative control. Hereinafter, mouse IgM is referred to as a negative control antibody.

2. Results

Figure 12A:
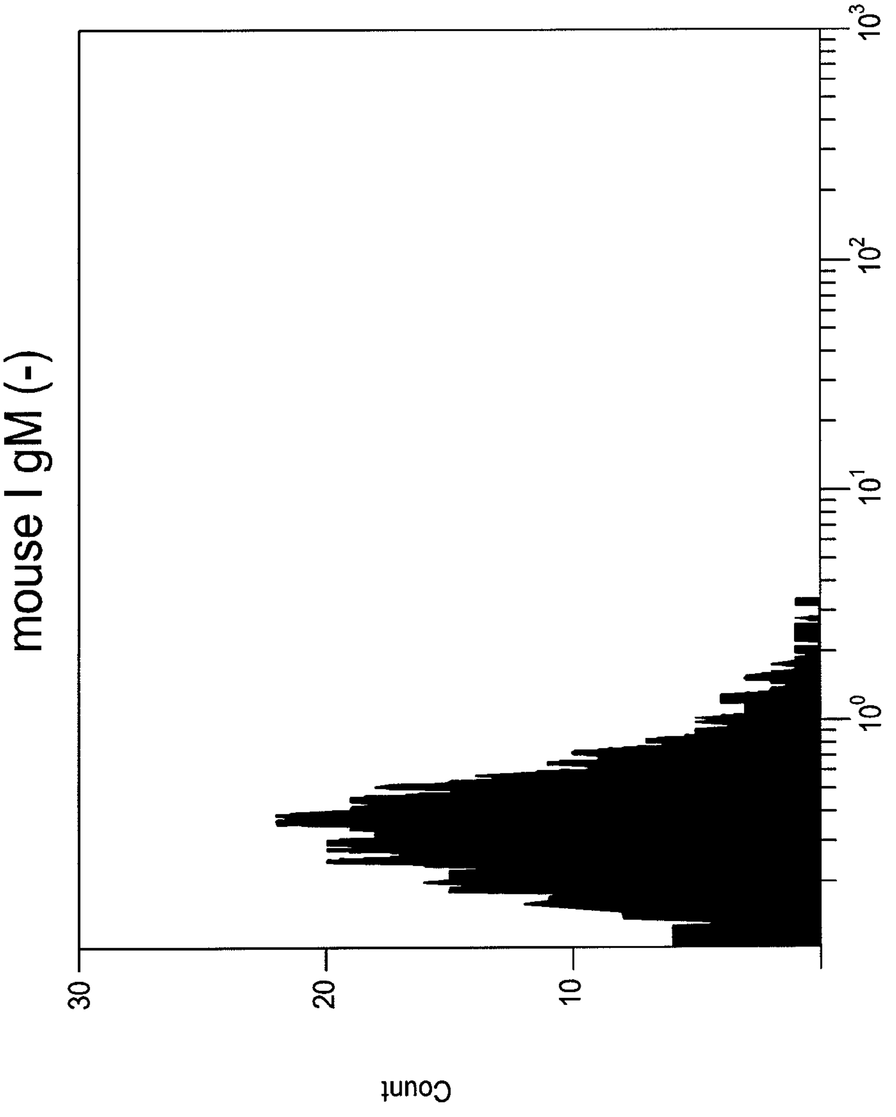
FIG. 12 Diagrams showing the results of detection of HS on cell surfaces by the flow cytometry method. The symbol (+) represents the use of HS-negative cells (heparitinase I digestion), while the symbol (−) represents the use of HS-positive cells (no heparitinase I digestion). The graph (A) shows the reactivity of the negative control antibody to HS-positive cells, the graph (B) shows the reactivity of NAH46 antibody to HS-positive cells, and the graph (C) shows the reactivity of NAH46 antibody to HS-negative cells.
Figure 12B:
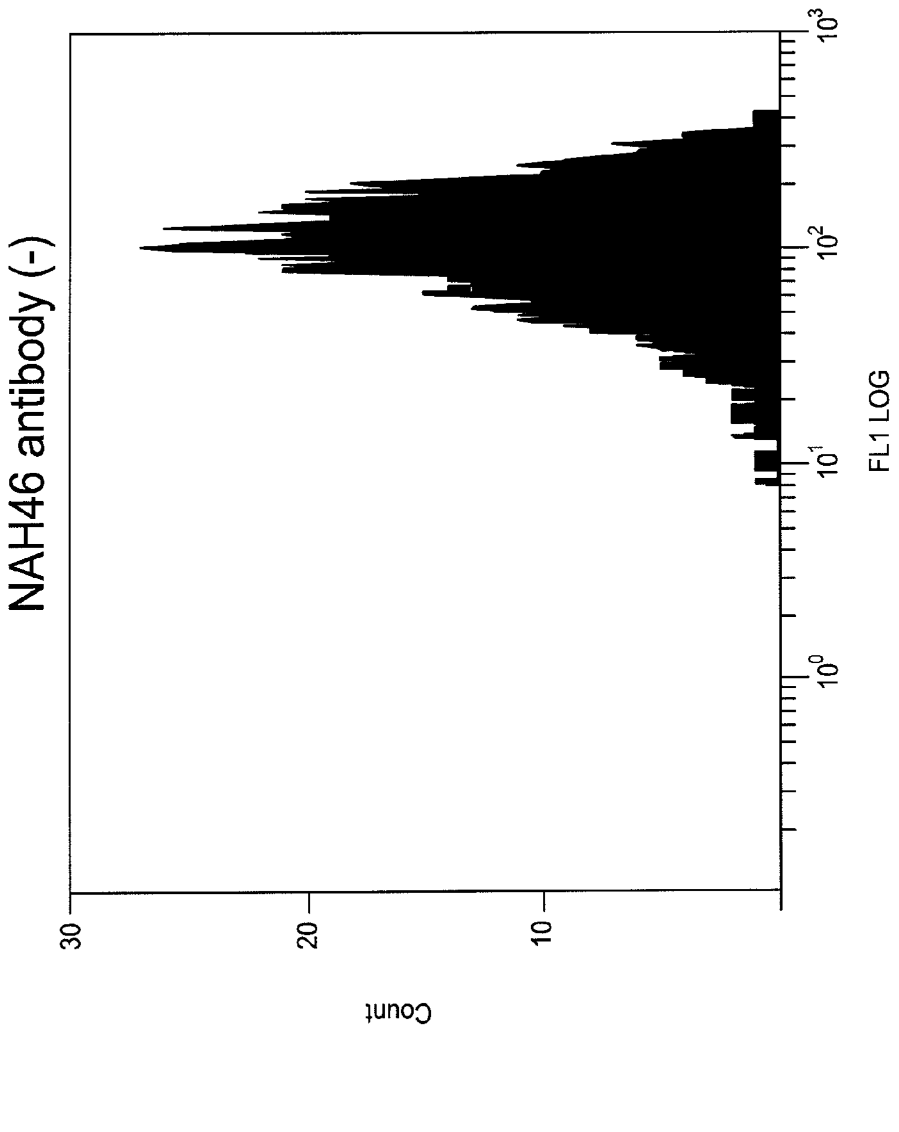

The negative control antibody did not react with the HS-positive cells (FIG. 12(A)), while NAH46 antibody reacted with the HS-positive cells (FIG. 12(B)) and detected HS on the surfaces of colo201 cells.

Figure 12C:
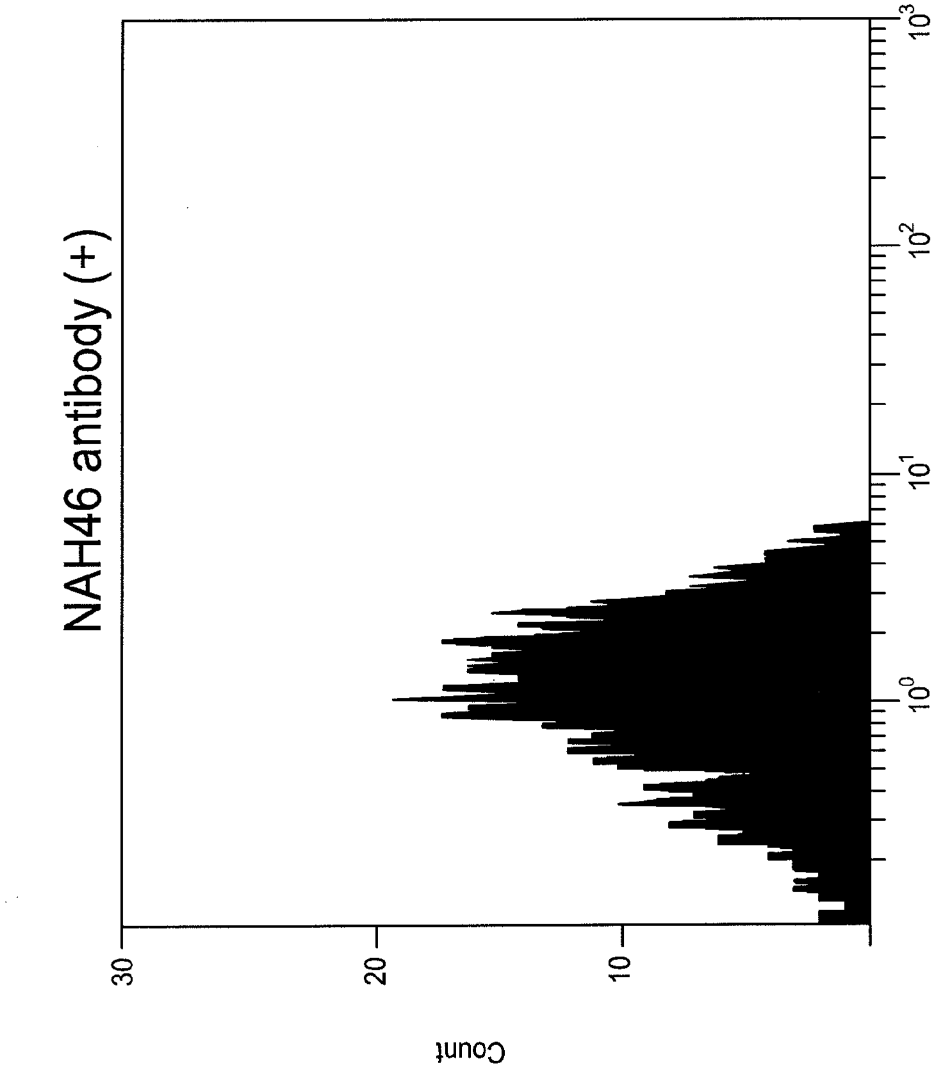

The negative-control antibody and NAH46 antibody did not react with the HS-negative cells (FIG. 12(C)). The results revealed that NAH46 antibody specifically recognized HS on the surfaces of colo201 cells.

As a result, it was clarified that the antibody of the present invention can specifically detect HS on the surfaces of cells.

INDUSTRIAL APPLICABILITY

The antibodies of the present invention reacts with NAH and bovine kidney HS and therefore can be suitably used for the detection of HS or NAH in a sample. Meanwhile, the antibodies of the present invention do not substantially react with mouse ESH-HS and therefore can specifically detect HS of low sulfation degree. In addition, the antibodies of the present invention can specifically recognize nonsulfated region of HS, which is composed of N-acetylglucosamine units or glucosamine units, and therefore the antibodies of the present invention can be applied to specific detection of the above-mentioned structures.

What is claimed is:

1. A hybridoma which has the Deposition number of FERM BP-10534, FERM BP-10535, or FERM BP-10536.

2. An isolated monoclonal antibody, which is produced by the hybridoma having Deposition number of FERM BP-10534, FERM BP-10535, or FERM BP-10536.

3. A kit for detecting heparan sulfate or N-acetylheparosan in a sample, comprising at least one antibody according to claim 2.

4. A method of detecting heparan sulfate or N-acetylheparosan in a sample, comprising:

contacting the sample with the antibody according to claim 2; and detecting the antibody bound to the heparan sulfate or N-acetylheparosan.

5. The detecting method according to claim 4, wherein the sample is derived from a source selected from the group consisting of body fluids, cells, tissues, and cultures of cells or microorganisms.

* * * * *

UNITED STATES PATENT AND TRADEMARK OFFICE

CERTIFICATE OF CORRECTION

PATENT NO. : 7,842,500 B2
APPLICATION NO. : 11/909956
DATED : November 30, 2010
INVENTOR(S) : Suzuki et al.

It is certified that error appears in the above-identified patent and that said Letters Patent is hereby corrected as shown below:

Page 1, Column 2, Line 19, OTHER PUBLICATIONS, “GIcNAc]n Epitopes” should be changed to --GlcNAc]n Epitopes--

Page 1, Column 2, Line 5, ABSTRACT, “Engelbreath-Holm-Swarn” should be changed to --Engelbreth-Holm-Swarm--

Column 1, Line 30, “desulfated-N-acetylated” should be changed to --desulfated, N-acetylated--

Column 1, Line 33, “desulfated-N-acetylated” should be changed to --desulfated, N-acetylated--

Column 1, Line 40, “desulfated-N-acetylated” should be changed to --desulfated, N-acetylated--

Column 1, Line 62, “Proteoglycan-heparan” should be changed to --Proteoglycan heparan--

Column 14, Line 28, “Biotin-Labeled Gag” should be changed to --Biotin-Labeled GAG--

Column 15, Line 2, “Gag” should be changed to --GAG--

Column 16, Line 61, “using glycosaminoglyean” should be changed to --using glycosaminoglycan--

Column 17, Lines 41-42, “In the above-mentioned table, “N.D” means below the detection limit.” should be deleted Column 18, Line 6, “Bi-Gag-immobilized” should be changed to --Bi-GAG-immobilized--

Column 27, Line 38, “Detection of Hs on” should be changed to --Detection of HS on--

Signed and Sealed this
Twenty-second Day of November, 2011

David J. Kappos
*Director of the United States Patent and Trademark Office*